US011266685B2

(12) United States Patent
Piergallini et al.

(10) Patent No.: US 11,266,685 B2
(45) Date of Patent: Mar. 8, 2022

(54) SILICONE-BASED BIOPHOTONIC COMPOSITIONS AND USES THEREOF

(71) Applicant: KLOX Technologies Inc., Laval (CA)

(72) Inventors: Remigio Piergallini, Grottammare (IT); Nikolaos Loupis, Athens (GR); Joanna Jaworska, Montreal (CA); Emmanuelle Devemy, Montreal (CA); Éric DesRosiers, Outremont (CA); Abdellatif Chenite, Kirkland (CA)

(73) Assignee: KLOX TECHNOLOGIES INC., Laval (CA)

( * ) Notice: Subject to any disclaimer, the term of this patent is extended or adjusted under 35 U.S.C. 154(b) by 0 days.

(21) Appl. No.: 15/317,316

(22) PCT Filed: Jun. 9, 2015

(86) PCT No.: PCT/IB2015/001761
§ 371 (c)(1),
(2) Date: Dec. 8, 2016

(87) PCT Pub. No.: WO2015/189712
PCT Pub. Date: Dec. 17, 2015

(65) Prior Publication Data
US 2017/0209484 A1 Jul. 27, 2017

Related U.S. Application Data

(60) Provisional application No. 62/009,870, filed on Jun. 9, 2014.

(51) Int. Cl.
| | |
|---|---|
| *A61K 31/80* | (2006.01) |
| *A61K 8/41* | (2006.01) |
| *A61K 8/46* | (2006.01) |
| *A61K 8/86* | (2006.01) |
| *A61K 8/891* | (2006.01) |
| *A61K 9/00* | (2006.01) |
| *A61K 41/00* | (2020.01) |
| *A61K 47/10* | (2017.01) |
| *A61N 5/06* | (2006.01) |
| *A61K 31/352* | (2006.01) |
| *A61K 8/73* | (2006.01) |

(Continued)

(52) U.S. Cl.
CPC ............. *A61K 31/80* (2013.01); *A61K 8/416* (2013.01); *A61K 8/463* (2013.01); *A61K 8/498* (2013.01); *A61K 8/731* (2013.01); *A61K 8/86* (2013.01); *A61K 8/891* (2013.01); *A61K 8/895* (2013.01); *A61K 8/90* (2013.01); *A61K 9/0014* (2013.01); *A61K 31/352* (2013.01); *A61K 41/00* (2013.01); *A61K 41/008* (2013.01); *A61K 47/10* (2013.01); *A61K 47/20* (2013.01); *A61L 26/0061* (2013.01); *A61L 26/0095* (2013.01); *A61N 5/062* (2013.01); *A61N 5/0616* (2013.01); *A61Q 19/00* (2013.01); *A61Q 19/08* (2013.01); *A61K 9/1075* (2013.01); *A61K 9/7015* (2013.01); *A61K 47/34* (2013.01); *A61K 2800/434* (2013.01); *A61K 2800/48* (2013.01); *A61K 2800/52* (2013.01); *A61K 2800/596* (2013.01); *A61K 2800/81* (2013.01); *A61N 2005/0651* (2013.01); *A61N 2005/0662* (2013.01)

(58) Field of Classification Search
CPC ........ A61K 31/80; A61K 8/416; A61K 8/463; A61K 8/498; A61K 8/731; A61K 8/86; A61K 8/891; A61K 8/895; A61K 8/90; A61K 9/0014; A61K 31/352; A61K 41/00; A61K 41/008; A61K 47/10; A61K 47/20; A61K 9/1075; A61K 9/7015; A61K 47/34; A61K 2800/434; A61K 2800/48; A61K 2800/52; A61K 2800/596; A61K 2800/81; A61L 26/0061; A61L 26/0095; A61N 5/0616; A61N 5/062; A61N 2005/0651; A61N 2005/0662; A61Q 19/00; A61Q 19/08; A61P 17/00; A61P 17/02; A61P 17/06; A61P 17/10; A61P 29/00
See application file for complete search history.

(56) References Cited

U.S. PATENT DOCUMENTS

| | | |
|---|---|---|
| 3,141,321 A | 7/1964 | Nicholas |
| 4,402,959 A | 9/1983 | Dybas et al. |

(Continued)

FOREIGN PATENT DOCUMENTS

| | | |
|---|---|---|
| CA | 2408323 A1 | 11/2001 |
| CA | 2902363 A1 | 9/2014 |

(Continued)

OTHER PUBLICATIONS

Brick et al., High tear strength silicone elastomers with low hardness and high elongation. International SAMPE Technical Conference, pp. 1-10. (Year: 2012).*

(Continued)

*Primary Examiner* — Abigail Vanhorn
(74) *Attorney, Agent, or Firm* — BCF LLP

(57) ABSTRACT

The present disclosure provides silicone-based biophotonic compositions and methods useful in phototherapy. In particular, the silicone-based biophotonic compositions of the present disclosure include a silicone phase and a surfactant phase, wherein the surfactant phase comprises at least one chromophore solubilized in a surfactant. The silicone-based biophotonic compositions and the methods of the present disclosure are useful for promoting wound healing and scarring, as well as various other skin disorders.

17 Claims, 6 Drawing Sheets

(51) Int. Cl.
*A61K 8/90* (2006.01)
*A61K 8/895* (2006.01)
*A61Q 19/08* (2006.01)
*A61L 26/00* (2006.01)
*A61K 8/49* (2006.01)
*A61Q 19/00* (2006.01)
*A61K 47/20* (2006.01)
*A61K 47/34* (2017.01)
*A61K 9/107* (2006.01)
*A61K 9/70* (2006.01)

(56) References Cited

U.S. PATENT DOCUMENTS

| | | | |
|---|---|---|---|
| 4,430,381 A | 2/1984 | Harvey et al. | |
| 4,533,435 A | 8/1985 | Intili | |
| 4,625,026 A | 11/1986 | Kim | |
| 4,736,467 A | 4/1988 | Schwarze et al. | |
| 4,855,139 A | 8/1989 | Srinivasan | |
| 4,917,892 A * | 4/1990 | Speaker | A61K 9/0014 424/401 |
| 5,069,907 A | 12/1991 | Mixon et al. | |
| 5,091,102 A | 2/1992 | Sheridan | |
| 5,529,769 A | 6/1996 | Cho et al. | |
| 5,534,246 A * | 7/1996 | Herb | A61K 8/042 424/65 |
| 5,639,464 A | 6/1997 | Terry et al. | |
| 5,853,883 A | 12/1998 | Nohr et al. | |
| 5,854,147 A | 12/1998 | Nohr et al. | |
| 5,885,557 A | 3/1999 | Lentini | |
| 5,894,042 A | 4/1999 | Ferralli | |
| 5,894,043 A | 4/1999 | Sood | |
| 5,919,554 A | 7/1999 | Watterson et al. | |
| 6,203,805 B1 | 3/2001 | Collins et al. | |
| 7,598,291 B2 | 10/2009 | Nimni et al. | |
| 7,722,904 B2 | 5/2010 | Schneider et al. | |
| 2004/0009227 A1 | 1/2004 | Tao | |
| 2006/0247313 A1 | 11/2006 | Murakami et al. | |
| 2007/0020217 A1 * | 1/2007 | Themens | A61K 8/345 424/70.12 |
| 2008/0108681 A1 | 5/2008 | Scimera et al. | |
| 2009/0069217 A1 | 3/2009 | Kato et al. | |
| 2009/0220450 A1 | 9/2009 | Green et al. | |
| 2009/0286886 A1 * | 11/2009 | Fisher | A61L 24/0042 514/772.3 |
| 2009/0325885 A1 | 12/2009 | Miyata et al. | |
| 2010/0104520 A1 * | 4/2010 | Candau | A61K 8/042 424/59 |
| 2010/0266989 A1 * | 10/2010 | Piergallini | A61K 8/22 433/215 |
| 2011/0081530 A1 | 4/2011 | Robinson et al. | |
| 2011/0086060 A1 | 4/2011 | Bidamant et al. | |
| 2011/0130459 A1 | 6/2011 | Spencer | |
| 2012/0134951 A1 * | 5/2012 | Stasko | A61K 9/0014 424/78.06 |

FOREIGN PATENT DOCUMENTS

| | | |
|---|---|---|
| CA | 2916337 A1 | 1/2015 |
| CN | 102300587 A | 12/2011 |
| CN | 102480969 A | 5/2012 |
| GB | 2499921 A * | 9/2013 ............ A61K 41/00 |
| JP | H09505066 A | 5/1997 |
| JP | H11506769 A | 6/1999 |
| JP | 2005-034353 A | 2/2005 |
| JP | 2005527493 A | 9/2005 |
| WO | 9513792 A1 | 5/1995 |
| WO | 9639116 A1 | 12/1996 |
| WO | 01/58452 A1 | 8/2001 |
| WO | 2003061696 A2 | 7/2003 |
| WO | 2010051636 A1 | 5/2010 |
| WO | 2011006100 A1 | 1/2011 |
| WO | 2011108520 A1 | 9/2011 |
| WO | 2001085212 A2 | 11/2011 |
| WO | 2012119131 A1 | 9/2012 |
| WO | 2013155620 A1 | 10/2013 |
| WO | 2014040176 A1 | 3/2014 |
| WO | 2014040177 A1 | 3/2014 |
| WO | 2014138930 A1 | 9/2014 |
| WO | 2015000058 A1 | 1/2015 |

OTHER PUBLICATIONS

SYLGARD®, "184 Silicone Elastomer Product Information Sheet", [Online], Apr. 2, 2014, Retrieved from the Internet URL: http://www.dowcomine.com/DataFiles/090276fe80190b08.pdf.
Curtis et al., "Medical applications of silicones", Biomaterials Sciences, An Introduction to Materials in Medicine.
Database GNPD, [Online] MINTEL, Nov. 30, 2010, "Photo dynamic therapy SPF 30", accession No. 1442681, XP002775115.
Supplementary European Search Report of European Patent Application No. 15806945.0; dated Oct. 31, 2017; Munich; Olausson Boulois, J.
International Search Report of PCT/IB2015/001761, dated Jan. 28, 2016, Wesley Sharman.
Office Action issued from the Japanese Patent Office dated Dec. 3, 2019.
Office Action issued from the European Patent Office dated Dec. 10, 2019.
English abstract provided for JP 2005-034353.
Avouac et al.. Inhibition of activator protein 1 signaling abrogates transforming growth factor b-mediated activation of fibroblasts and prevents experimental fibrosis, Arthritis Rheumatism, 2012, vol. 64: 1642-1652.
Beyer et al., Tyrosine kinase signaling in fibrotic disorders, Translation of basic research to human disease, Biochem Biophys Acta, 2013, vol. 1832: 897-904.
Chen et al.. Focus on collagen: In vitro systems to study fibrogenesis and antifibrosis—state of the art, Fibrogenesis Tissue Repair, 2009, vol. 2: 7.
Cutroneo, TGF-beta-induced fibrosis and SMAD signaling, oligo decoys as natural therapeutics for inhibition of tissue and scarring, Wound Rep Regen 2007, vol. 15, S54-60.
Gauglitz et al.. Hypertrophic scarring and keloids: pathomechanisms and current and emerging treatment strategies, Mol Med, 2011, vol. 17:113-125.
Momtazi et al., A nude mouse model of hypertophic scar shows morphologic and histologic characteristics of human hypertrophic scar, Wound Rep Reg, 2013, vol. 21: 77-87.
Trojanowska, Role of PDGF in fibrotic diseases and systemic sclerosis, Rheumatology, 2008, vol. 47, v2-v4.

* cited by examiner

Figure 1. Light emission spectra of biophotonic silicone-thermogel during 0-5 minutes of illumination Figure 2. Light emission spectra of biophotonic silicone-thermogel during 5-10 minutes of illumination

| Thermogel/Sillicone | | mW/cm2 at 5cm | | | | | | | | | | | | |
|---|---|---|---|---|---|---|---|---|---|---|---|---|---|---|
| 15 mins | | 0 | 0,5 min | 1 min | 1,5 min | 2 min | 2,5 min | 3 min | 3,5 min | 4 min | 4,5 min | 5 min | J/cm2 | |
| Lamp | 400-518 | 67.38 | 67.43 | 67.64 | 67.77 | 67.89 | 68.05 | 67.99 | 68.07 | 68.14 | 68.12 | 68.00 | 20.36 | 98.7% |
| Fluoresc. | 519-760 | 0.91 | 0.92 | 0.90 | 0.88 | 0.86 | 0.87 | 0.84 | 0.83 | 0.82 | 0.8 | 0.78 | 0.23 | 1.3% |
| total | 400-760 | 68.29 | 68.35 | 68.54 | 68.64 | 68.74 | 68.92 | 68.63 | 68.89 | 68.96 | 68.91 | 68.78 | 20.61 | 100.0% |
| % fluorescence | | 1.3% | 1.3% | 1.3% | 1.3% | 1.3% | 1.3% | 1.2% | 1.2% | 1.2% | 1.2% | 1.1% | 0.001 | 1.3% |
| Purple | (400)-450 | 42.66 | 41.92 | 41.81 | 41.66 | 41.48 | 41.44 | 41.29 | 41.26 | 41.1 | 40.98 | 40.81 | 12.46 | 60.5% |
| Blue | 450-500 | 24.71 | 23.49 | 25.8 | 26.1 | 26.37 | 26.57 | 26.71 | 26.87 | 27.00 | 27.1 | 27.15 | 7.88 | 38.2% |
| Green | 500-570 | 0.45 | 0.45 | 0.44 | 0.48 | 0.48 | 0.44 | 0.42 | 0.41 | 0.41 | 0.39 | 0.39 | 0.13 | 0.6% |
| Yellow | 570-591 | 0.30 | 0.31 | 0.31 | 0.29 | 0.29 | 0.29 | 0.28 | 0.28 | 0.28 | 0.27 | 0.27 | 0.09 | 0.4% |
| Orange | 591-610 | 0.14 | 0.14 | 0.14 | 0.13 | 0.13 | 0.13 | 0.13 | 0.13 | 0.13 | 0.13 | 0.12 | 0.04 | 0.2% |
| Red | 610-760 | 0.02 | 0.02 | 0.02 | 0.02 | 0.02 | 0.02 | 0.02 | 0.02 | 0.02 | 0.02 | 0.02 | 0.01 | 0.0% |
| total | 400-700 | 68.3 | 68.36 | 68.56 | 68.65 | 68.75 | 68.93 | 68.84 | 68.9 | 68.97 | 68.92 | 68.78 | 20.62 | 100.0% |

Figure 3

Figure 4. Photobleaching of biophotonic silicone-thermogel over the indicated time period

SILICONE-BASED BIOPHOTONIC COMPOSITIONS AND USES THEREOF

CROSS-REFERENCE TO RELATED APPLICATIONS

This application is a national stage application under 35 U.S.C. § 371 of International Application No. PCT/IB2015/001761, filed Jun. 9, 2015, which claims the benefit of and priority to U.S. Provisional Patent Application No. 62/009,870 filed Jun. 9, 2014, which is incorporated by reference herein in its entirety. International Application PCT/IB2015/001761 was published under PCT Article 21(2) in English.

BACKGROUND OF THE DISCLOSURE

Phototherapy has recently been recognized as having wide range of applications in both the medical and cosmetic fields including use in surgery, therapy and diagnostics. For example, phototherapy has been used to treat cancers and tumors with lessened invasiveness, to disinfect target sites as an antimicrobial treatment, to promote wound healing, and for facial skin rejuvenation.

Photodynamic therapy is a type of phototherapy involving the application of a photosensitive agent to target tissue then exposing the target tissue to a light source after a determined period of time during which the photosensitizer is absorbed by the target tissue. Such regimens, however, are often associated with undesired side-effects, including systemic or localized toxicity to the patient or damage to non-targeted tissue. Moreover, such existing regimens often demonstrate low therapeutic efficacy due to, for example, the poor selectivity of the photosensitive agents into the target tissues.

Silicones are compounds based on alkylsiloxane or organosiloxane and include polydimethylenesiloxane (PDMS), that have been recognized as biocompatible and have been successfully used in medical applications over the last six decades (Curtis et al., In *Biomaterials Science* $2^{nd}$ Edition, 2004). PDMS-based compositions are widely used in personal care and skin topical applications because they are non-irritating, non-sensitizing, and meet the strict standards imposed by the US and European regulatory agencies.

Therefore, it is an object of the present disclosure to provide new and improved silicone based-compositions useful in phototherapy and methods for their use.

SUMMARY OF THE DISCLOSURE

The present disclosure provides silicone-based biophotonic compositions and methods useful in phototherapy. In particular, the biophotonic compositions of the present disclosure include a silicone matrix, and at least one chromophore, wherein the at least one chromophore can absorb and emit light from within the biophotonic composition, and which may be useful for cosmetic or medical treatment of a human or animal tissue.

In one aspect, there is provided a silicone-based biophotonic composition comprising a silicone phase and a surfactant phase, wherein the surfactant phase comprises at least one chromophore solubilized in a surfactant. In some embodiments, the surfactant phase is emulsified in the silicone phase. In certain embodiments, the silicone phase is a continuous phase. In some embodiments, the surfactant is a block copolymer. The block copolymer may comprise at least one hydrophobic block and at least one hydrophilic block. In some embodiments the surfactant is thermogellable.

In certain embodiments of any of the foregoing or following, the surfactant comprises at least one sequence of polyethylene glycol-polypropylene glycol ((PEG)-(PPG)). In a further embodiment the surfactant is a triblock copolymer or poloxomer of the formula (PEG)-(PPG)-(PEG). In yet another embodiment, the surfactant is Pluronic F127.

In certain embodiments of any of the foregoing or following, the surfactant comprises at least one sequence of polyethylene glycol-polylactic acid ((PEG)-(PLA)). In some embodiments the surfactant comprises at least one sequence of polyethyelene glycol-poly(lactic-c -glycolic acid) ((PEG)-(PLGA)). In some embodiments the surfactant comprises at least one sequence of polyethyelene glycol-polycaprolactone ((PEG)-(PCL)). In a further embodiment the surfactant is a triblock copolymer or poloxomer of the formula A-B-A or B-A-B, wherein A is PEG and B is PLA or PLGA or PCL.

In certain embodiments of any of the foregoing or following, the silicone phase comprises silicone. In certain embodiments, the silicone may be a silicone elastomer. In certain embodiments, the silicone comprises a polydimethylsiloxane. In certain embodiments, the silicone comprises Sylgard® 184. In certain embodiments the silicone comprises a mixture of Sylgard® 184 and Sylgard® 527. In a further embodiment the silicone comprises a mixture of about 15% Sylgard® 184 and about 85% Sylgard® 527. In certain embodiments, the mixture of Sylgard® 184 and Sylgard® 527 provides for a silicone-based biophotonic composition in a membrane form having an elasticity and a tackiness which may be well suited to skin applications. Specifically, the elasticity may allow for a greater ease of manipulation of the silicone-based biophotonic membrane, and the tackiness (stickiness) may allow for the membrane to stay where it is placed during a treatment procedure as may be provided for in the present disclosure.

In certain embodiments of any of the foregoing or following, the silicone-based biophotonic composition comprises 80 wt % silicone phase and about 20 wt % surfactant phase. In some embodiments the silicone-based biophotonic compsotion comprises a silicone phase/surfactant phase wt % composition of about 60/40 wt %, or about 65/55 wt %, or about 70/30 wt %, or about 75/25 wt %, or about 80/20 wt %, or about 85/15 wt % or about 90/10 wt %.

In certain embodiments of any of the foregoing or following, the at least one chromophore is water soluble and is solubilized in the surfactant phase. The at least one chromophore may be a fluorophore. In certain embodiments, the chromophore can absorb and/or emit light. In some embodiments, the light absorbed and/or emitted by the chromophore is in the visible range of the electromagnetic spectrum. In some embodiments, the light absorbed and/or emitted by the chromophore is in the range of about 400 nm to about 750 nm. In certain embodiments, the chromophore can emit light from around 500 nm to about 700 nm. In some embodiments, the chromophore or the fluorophore is a xanthene dye. The xanthene dye may be selected from Eosin Y, Eosin B, Erythrosine B, Fluorescein, Rose Bengal and Phloxin B.

In certain embodiments of any of the foregoing or following, the surfactant phase of the silicone-based biophotonic composition further comprises a stabilizer. In further embodiments the stabilizer comprises gelatin, hydroxyethyl cellulose ether (HEC), carboxymethyl cellulose (CMC) or any other thickening agent.

In certain embodiments of any of the foregoing or following, the silicone-based biophotonic composition is at least substantially translucent. The silicone-based biophotonic composition may be transparent. In some embodiments, the silicone-based biophotonic composition has a translucency of at least about 40%, about 50%, about 60%, about 70%, or about 80% in a visible range. Preferably, the light transmission through the composition is measured in the absence of the at least one chromophore.

In certain embodiments, the composition is in the form of a membrane. In other embodiments, the composition is in the form of a spreadable gel.

In certain embodiments of any of the foregoing or following, the surfactant phase further comprises an oxidizing agent. The oxidizing agent may comprise a peroxide, such as hydrogen peroxide, urea peroxide and benzoyl peroxide, or any other oxidizing agent which can modulate the light absorption and/or emission properties of the at least one chromophore or which can oxidize or degrade the chromophore. For example, in certain embodiments where a single use of the composition is desired, a peroxide may be included in the surfactant phase to ensure degradation of the at least one chromophore within a single treatment time.

In certain embodiments of any of the foregoing or following, the silicone-based biophotonic composition, for example in the form of a silicone-based biophotonic membrane, has a thickness of about 0.1 mm to about 50 mm, about 0.5 mm to about 20 mm, or about 1 mm to about 10 mm, or about 1 mm to about 5 mm. In some embodiments, the biophotonic composition is in the form of a gel that is applied at a thickness of about 0.1 mm to about 50 mm, about 0.5 mm to about 20 mm, or about 1 mm to about 10 mm, or about 1 mm to about 5 mm.

In certain embodiments of any of the foregoing or following, the silicone-based composition, for example in the form of a silicone-based biophotonic membrane, has a removeable cover for covering one or both sides of the membrane. The removeable cover may be peelable. The removeable cover may comprise a sheet or a film of material, such as paper or foil. In certain embodiments, the removeable cover is opaque and can protect the membrane from illumination until the treatment time. The cover may be partially removeable. In certain embodiments, the cover may be re-applicable to the membrane surface, such as after a treatment time, in order to protect the membrane from further illumination in between treatments.

In certain embodiments of any of the foregoing or following, the surfactant phase is homogenously distributed within the silicone phase and is nano and/or micro-sized. It can be considered as micro-emulsified. The surfactant phase is not visibly detectable by eye. In other words, the membrane appears by eye as one phase.

The silicone-based biophotonic composition of any aspects or embodiments of the disclosure may be used for cosmetic or medical treatment of tissue. In some embodiments, the cosmetic treatment is skin rejuvenation and conditioning, and the medical treatment is wound healing, periodontal treatment or acne treatment or treatment of other skin conditions including eczema, psoriasis or dermatitis. In some aspects, the silicone-based biophotonic membrane is used for modulating inflammation, for modulating collagen synthesis, or for promoting angiogenesis.

The present disclosure also provides methods for biophotonic treatment comprising applying the silicone-based biophotonic composition of the disclosure to a target tissue and illuminating the composition with light.

From one aspect, there is provided a method for biophotonic treatment of a skin disorder wherein the method comprises placing a silicone-based biophotonic composition of the disclosure on or over a target skin tissue, and illuminating said silicone-based biophotonic composition with light having a wavelength that overlaps with an absorption spectrum of the at least one chromophore. In some embodiments, the biophotonic composition emits fluorescence at a wavelength and intensity that promotes healing of said skin disorder. The skin disorder may be selected from eczema, psoriasis or dermatitis.

From another aspect, there is provided a method for biophotonic treatment of acne comprising: placing a silicone-based biophotonic composition of the disclosure on or over a target skin tissue; and illuminating said composition with light having a wavelength that overlaps with an absorption spectrum of the at least one chromophore. In some embodiments, the biophotonic composition emits fluorescence at a wavelength and intensity that treats the acne.

From another aspect, there is provided a method for promoting wound healing comprising: placing a silicone-based biophotonic composition of the disclosure on or over a wound and illuminating said silicone-based biophotonic composition with light having a wavelength that overlaps with an absorption spectrum of the at least one chromophore. In some embodiments, the biophotonic composition emits fluorescence at a wavelength and intensity that promotes wound healing.

From another aspect, there is provided a method for biophotonic tissue repair comprising: placing a silicone-based biophotonic composition of the disclosure on or over a target tissue; and illuminating said silicone-based biophotonic composition with light having a wavelength that overlaps with an absorption spectrum of the at least one chromophore. In some embodiments, the biophotonic composition emits fluorescence at a wavelength and intensity that promotes tissue repair.

From another aspect, there is provided a method for promoting skin rejuvenation comprising: placing a silicone-based biophotonic composition of the disclosure on or over a target skin tissue; and illuminating said silicone-based biophotonic composition with light having a wavelength that overlaps with an absorption spectrum of the at least one chromophore. In some embodiments, the biophotonic composition emits fluorescence at a wavelength and intensity that promotes skin rejuvenation. Promoting skin rejuvenation may comprise promoting collagen synthesis.

From another aspect, there is provided a method for preventing or treating scarring comprising: placing a silicone-based biophotonic composition of the disclosure on or over a tissue scar; and illuminating said silicone-based biophotonic composition with light having a wavelength that overlaps with an absorption spectrum of the at least one chromophore. In some embodiments, silicone-based biophotonic composition emits fluorescence at a wavelength and intensity that diminishes or prevents scarring.

In certain embodiments, the silicone-based biophotonic composition is left in place after illumination. In certain embodiments, the silicone-based biophotonic composition is re-illuminated. In some embodiments, the chromophore at least partially photobleaches during or after illumination. In certain embodiments, the silicone-based biophotonic composition is illuminated until the chromophore is at least partially photobleached.

In certain embodiments of any of the foregoing or following, the light has a peak wavelength between about 400 nm and about 750 nm. The light may have a peak wavelength between about 400 nm and about 500 nm.

In certain embodiments of any of the foregoing or following, the light is from a direct light source such as a lamp. The lamp may be an LED lamp. In certain embodiments, the light is from an ambient light source.

In certain embodiments of any of the foregoing or following, said silicone-based biophotonic composition is illuminated by a direct light source for about 1 minute to greater than 75 minutes, about 1 minute to about 75 minutes, about 1 minute to about 60 minutes, about 1 minute to about 55 minutes, about 1 minute to about 50 minutes, about 1 minute to about 45 minutes, about 1 minute to about 40 minutes, about 1 minute to about 35 minutes, about 1 minute to about 30 minutes, about 1 minute to about 25 minutes, about 1 minute to about 20 minutes, about 1 minute to about 15 minutes, about 1 minute to about 10 minutes, or about 1 minute to about 5 minutes.

From a further aspect, there is provided use of the compositions described above for tissue repair; for wound healing; for preventing or treating scars; for skin rejuvenation; for treating skin conditions such as acne, eczema, psoriasis or dermatitis; for modulating inflammation; or for modulating collagen synthesis.

BRIEF DESCRIPTION OF THE DRAWINGS

Further aspects and advantages of the present invention will become better understood with reference to the description in association with the following in which:

FIG. 3 illustrates the light emission spectra of the membrane of FIG. 1 during 10-15 minutes of illumination.

DETAILED DESCRIPTION (1) Overview

Figure 1:
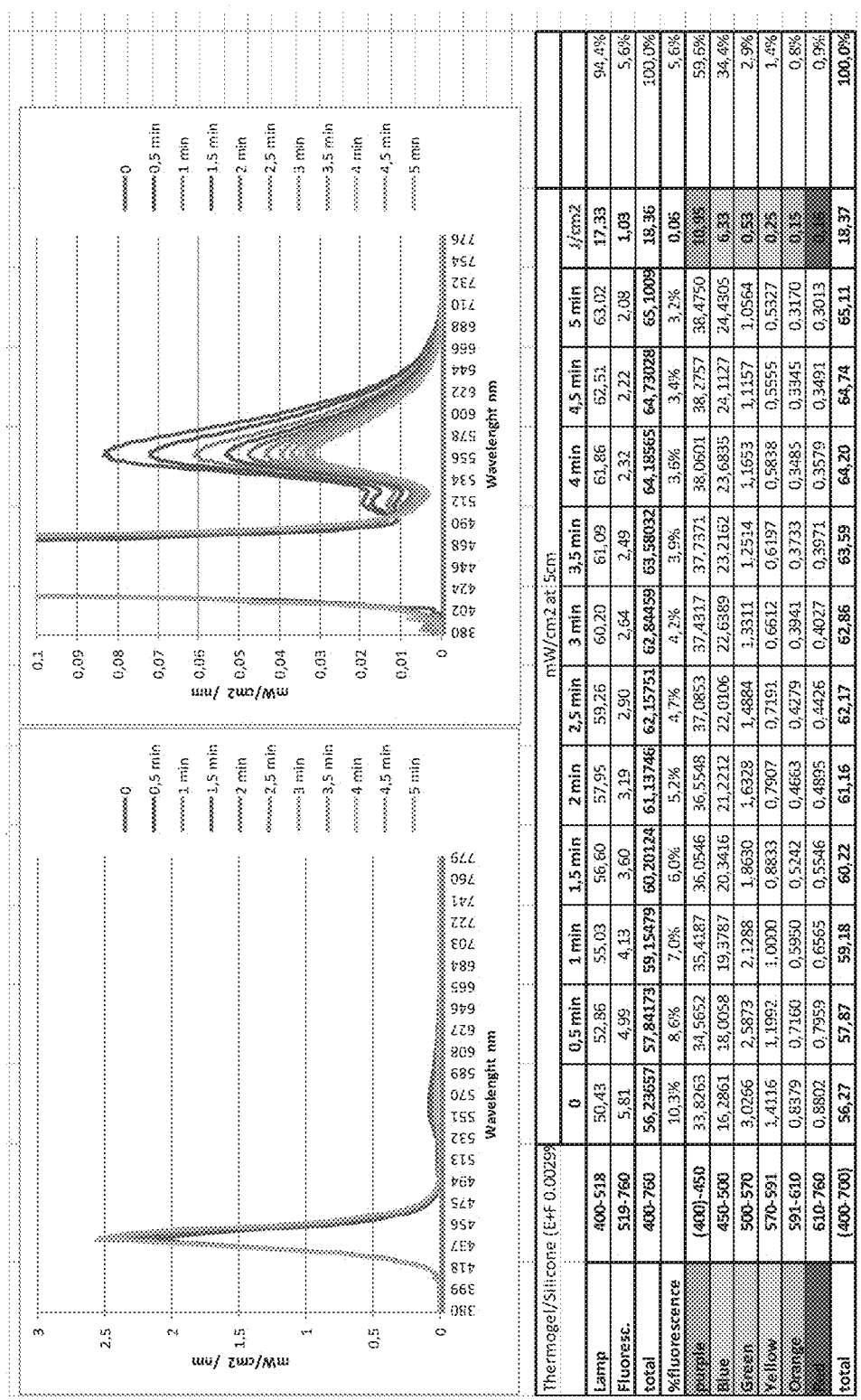
FIG. 1 illustrates the light emission spectra of one embodiment of the present disclosure comprising a silicone-based biophotonic composition in a form of a membrane during 0-5 minutes of illumination.
Figure 2:
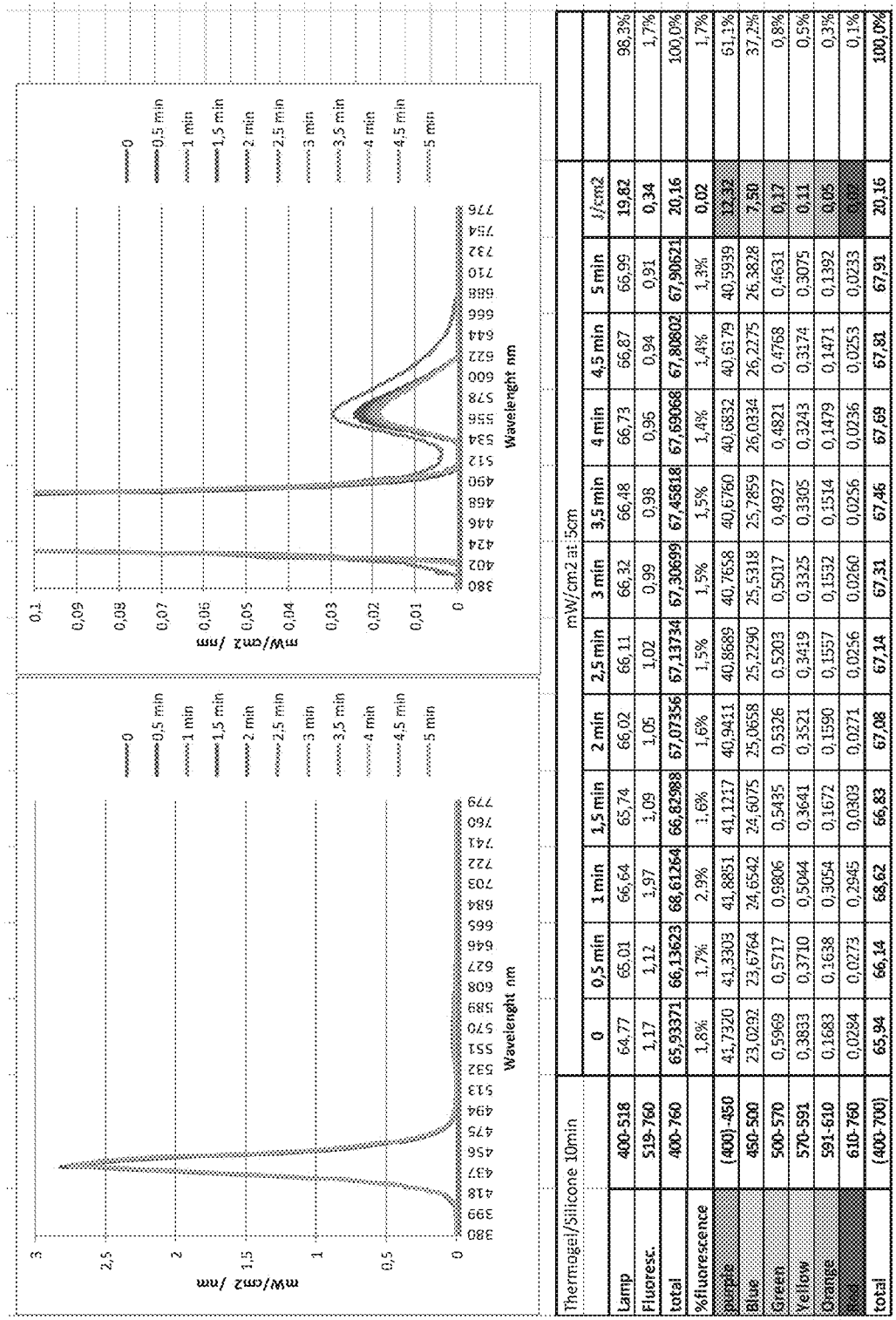
FIG. 2 illustrates the light emission spectra of the membrane of FIG. 1 during 5-10 minutes of illumination.
Figure 4:
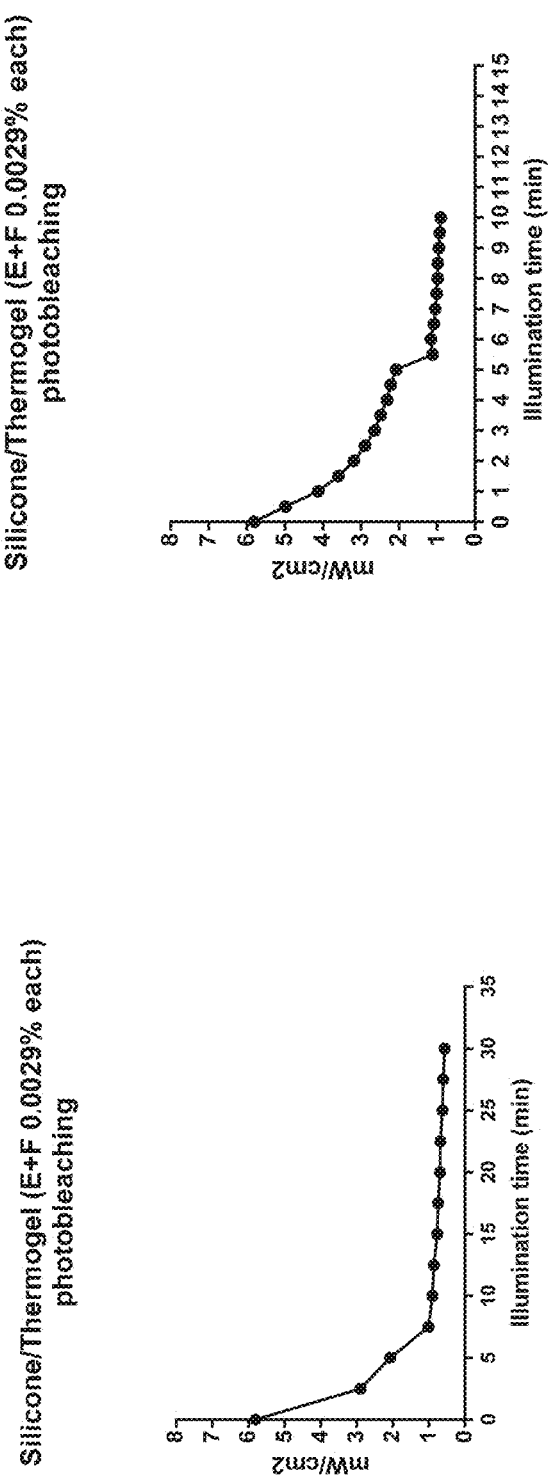
FIG. 4, panels A and B illustrate photobleaching of the membrane of FIG. 1 over the indicated time period.

The present disclosure provides silicone-based biophotonic compositions and uses thereof. Biophotonic therapy using these compositions would combine the beneficial effects of topical silicone compositions with the photobiostimulation induced by the fluorescent light generated by the chromophore(s) upon illumination of the compositions. Furthermore, in certain embodiments, phototherapy using the silicone-based biophotonic membranes of the present disclosure will for instance rejuvenate the skin by, e.g., promoting collagen synthesis, promote wound healing, prevent or treat scars or to treat a skin conditions such as acne, eczema, psoriasis, and treat periodontitis.

(2) Definitions

Before continuing to describe the present disclosure in further detail, it is to be understood that this disclosure is not limited to specific compositions or process steps, as such may vary. It must be noted that, as used in this specification and the appended claims, the singular form "a", "an" and "the" include plural referents unless the context clearly dictates otherwise.

As used herein, the term "about" in the context of a given value or range refers to a value or range that is within 20%, preferably within 10%, and more preferably within 5% of the given value or range.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

"Biophotonic" means the generation, manipulation, detection and application of photons in a biologically relevant context. In other words, biophotonic compositions exert their physiological effects primarily due to the generation and manipulation of photons.

"Topical application" or "topical uses" means application to body surfaces, such as the skin, mucous membranes, vagina, oral cavity, internal surgical wound sites, and the like.

"Emulsion" shall be understood as referring to a temporary or permanent dispersion of one liquid phase within a second liquid phase. Generally one of the phases is an aqueous solution, and the other a water-immiscible liquid. The water-immiscible liquid is generally referred to as the continuous phase. In this disclosure, the continuous phase comprises a silicone and is referred to as a silicone phase. Moreover, in this disclosure, the aqueous phase comprises a surfactant and is referred to as a surfactant phase.

Terms "chromophore" and "photoactivator" are used herein interchangeably. A chromophore means a chemical compound, when contacted by light irradiation, is capable of absorbing the light. The chromophore readily undergoes photoexcitation and can transfer its energy to other molecules or emit it as light (fluorescence).

"Photobleaching" or "photobleaches" means the photochemical destruction of a chromophore. A chromophore may fully or partially photobleach.

The term "actinic light" is intended to mean light energy emitted from a specific light source (e.g. lamp, LED, or laser) and capable of being absorbed by matter (e.g. the chromophore or photoactivator). Terms "actinic light" and "light" are used herein interchangeably. In a preferred embodiment, the actinic light is visible light.

"Skin rejuvenation" means a process of reducing, diminishing, retarding or reversing one or more signs of skin aging or generally improving the condition of skin. For instance, skin rejuvenation may include increasing luminosity of the skin, reducing pore size, reducing fine lines or wrinkles, improving thin and transparent skin, improving firmness, improving sagging skin (such as that produced by bone loss), improving dry skin (which might itch), reducing or reversing freckles, reducing or preventing the appearance of age spots, spider veins, rough and leathery skin, fine wrinkles that disappear when stretched, reducing loose skin, or improving a blotchy complexion. According to the present disclosure, one or more of the above conditions may be improved or one or more signs of aging may be reduced, diminished, retarded or even reversed by certain embodiments of the compositions, methods and uses of the present disclosure.

"Wound" means an injury to any tissue, including for example, acute, subacute, delayed or difficult to heal wounds, and chronic wounds. Examples of wounds may include both open and closed wounds. Wounds include, for example, amputations, burns, incisions, excisions, lesions, lacerations, abrasions, puncture or penetrating wounds, surgical wounds, amputations, contusions, hematomas, crushing injuries, ulcers (such as for example pressure, diabetic, venous or arterial), scarring, and wounds caused by periodontitis (inflammation of the periodontium).

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

(3) Silicone-Based Biophotonic Compositions

The present disclosure provides, in a broad sense, silicone-based biophotonic compositions and methods of using silicone-based biophotonic compositions. Silicone-based biophotonic compositions can be, in a broad sense, activated by light (e.g., photons) of specific wavelength. A silicone-based biophotonic composition according to various embodiments of the present disclosure comprises a silicone phase and a surfactant phase, with at least one chromophore solubilized in the surfactant phase. In some embodiments, the surfactant phase is emulsified in the silicone phase. The chromophore in the silicone-based biophotonic composition may be activated by light. This activation accelerates the dispersion of light energy, leading to light carrying on a therapeutic effect on its own, and/or to the photochemical activation of other agents contained in the composition (e.g., acceleration in the breakdown process of peroxide (an oxidant or oxidizing agent) when such compound is present in the composition or in contact with the composition, leading to the formation of oxygen radicals, such as singlet oxygen). This may lead to the breakdown of the chromophore and, in some embodiments, ensure that the silicone-based biophotonic composition, for example in the form of a membrane, is for single-use.

When a chromophore absorbs a photon of a certain wavelength, it becomes excited. This is an unstable condition and the molecule tries to return to the ground state, giving away the excess energy. For some chromophores, it is favorable to emit the excess energy as light when returning to the ground state. This process is called fluorescence. The peak wavelength of the emitted fluorescence is shifted towards longer wavelengths compared to the absorption wavelengths due to loss of energy in the conversion process. This is called the Stokes' shift. In the proper environment (e.g., in a biophotonic composition) much of this energy is transferred to the other components of the biophotonic composition or to the treatment site directly.

Without being bound to theory, it is thought that fluorescent light emitted by photoactivated chromophores may have therapeutic properties due to its femto-, pico-, or nano-second emission properties which may be recognized by biological cells and tissues, leading to favourable biomodulation. Furthermore, generally, the emitted fluorescent light has a longer wavelength and hence a deeper penetration into the tissue than the activating light. Irradiating tissue with such a broad range of wavelength, including in some embodiments the activating light which passes through the composition, may have different and complementary effects on the cells and tissues. In other words, chromophores are used in the silicone-based biophotonic compositions of the present disclosure for therapeutic effect on tissues. This is a distinct application of these photoactive agents and differs from the use of chromophores as simple stains or as catalysts for photo-polymerization.

The silicone-based biophotonic compositions of the present disclosure may have topical uses such as a mask or a wound dressing. In some embodiments, the silicone-based biophotonic compositions are cohesive. The cohesive nature of these silicone-based biophotonic compositions may provide ease of removal from the site of treatment and hence provide for a convenient ease of use. Additionally or alternatively, the silicone-based biophotonic compositions of the present disclosure have functional and structural properties and these properties may also be used to define and describe the compositions. Individual components of the silicone-based biophotonic compositions of the present disclosure, including chromophores, surfactants, silicone, and other optional ingredients, are detailed below.

(a) Chromophores

Suitable chromophores can be fluorescent compounds (or stains) (also known as "fluorochromes" or "fluorophores"). Other dye groups or dyes (biological and histological dyes, food colorings, carotenoids, and other dyes) can also be used. Suitable photoactivators can be those that are Generally Regarded As Safe (GRAS). Advantageously, photoactivators which are not well tolerated by the skin or other tissues can be included in the biophotonic composition of the present disclosure, as in certain embodiments, the photoactivators are encapsulated within the surfactant phase of the emulsion in the silicone continuous phase.

In certain embodiments, the chromophore is one which undergoes partial or complete photobleaching upon application of light. In some embodiments, the chromophore absorbs at a wavelength in the range of the visible spectrum, such as at a wavelength of about 380-800 nm, 380-700, 400-800, or 380-600 nm. In other embodiments, the chromophore absorbs at a wavelength of about 200-800 nm, 200-700 nm, 200-600 nm or 200-500 nm. In one embodiment, the chromophore absorbs at a wavelength of about 200-600 nm. In some embodiments, the chromophore absorbs light at a wavelength of about 200-300 nm, 250-350 nm, 300-400 nm, 350-450 nm, 400-500 nm, 450-650 nm, 600-700 nm, 650-750 nm or 700-800 nm.

It will be appreciated to those skilled in the art that optical properties of a particular chromophore may vary depending on the chromophore's surrounding medium. Therefore, as used herein, a particular chromophore's absorption and/or emission wavelength (or spectrum) corresponds to the wavelengths (or spectrum) measured in a biophotonic composition of the present disclosure.

The silicone-based biophotonic composition disclosed herein may include at least one additional chromophore or second chromophore. Combining chromophores may increase photo-absorption by the combined dye molecules and enhance absorption and photo-biomodulation selectivity. This creates multiple possibilities of generating new photosensitive, and/or selective chromophores mixtures. Thus, in certain embodiments, silicone-based biophotonic compositions of the disclosure include more than one chromophore, and when illuminated with light, energy transfer can occur between the chromophores. This process, known as resonance energy transfer, is a widely prevalent photophysical process through which an excited 'donor' chromophore (also referred to herein as first chromophore) transfers its excitation energy to an 'acceptor' chromophore (also referred to herein as second chromophore). The efficiency and directedness of resonance energy transfer depends on the spectral features of donor and acceptor chromophores. In particular, the flow of energy between chromophores is dependent on a spectral overlap reflecting the relative positioning and shapes of the absorption and emission spectra. More specifically, for energy transfer to occur, the emission spectrum of the donor chromophore must overlap with the absorption spectrum of the acceptor chromophore.

Energy transfer manifests itself through decrease or quenching of the donor emission and a reduction of excited state lifetime accompanied also by an increase in acceptor emission intensity. To enhance the energy transfer efficiency, the donor chromophore should have good abilities to absorb photons and emit photons. Furthermore, the more overlap there is between the donor chromophore's emission spectra and the acceptor chromophore's absorption spectra, the better a donor chromophore can transfer energy to the acceptor chromophore.

Accordingly, in embodiments comprising a mixture of chromophores, the first chromophore has an emission spectrum that overlaps at least about 80%, 50%, 40%, 30%, 20% or 10% with an absorption spectrum of the second chromophore. In one embodiment, the first chromophore has an emission spectrum that overlaps at least about 20% with an absorption spectrum of the second chromophore. In some embodiments, the first chromophore has an emission spectrum that overlaps at least 1-10%, 5-15%, 10-20%, 15-25%, 20-30%, 25-35%, 30-40%, 35-45%, 50-60%, 55-65%, 60-70% or 70-80% with an absorption spectrum of the second chromophore.

% spectral overlap, as used herein, means the % overlap of a donor chromophore's emission wavelength range with an acceptor chromophore's absorption wavelength rage, measured at spectral full width quarter maximum (FWQM). In some embodiments, the second chromophore absorbs at a wavelength in the range of the visible spectrum. In certain embodiments, the second chromophore has an absorption wavelength that is relatively longer than that of the first chromophore within the range of about 50-250, 25-150 or 10-100 nm.

The chromophore may be present in an amount of about 0.001-40% per weight of the composition or of the surfactant phase. In certain embodiments, the at least one chromophore is present in an amount of about 0.001-3%, 0.001-0.01%, 0.005-0.1%, 0.1-0.5%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the silicone-based biophotonic composition or of the surfactant phase.

When present, the second chromophore may be present in an amount of about 0.001-40% per weight of the silicone-based biophotonic composition or of the surfactant phase. In certain embodiments, the second chromophore is present in an amount of about 0.001-3%, 0.001-0.01%, 0.005-0.1%, 0.1-0.5%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the silicone-based biophotonic composition or of the surfactant phase. In certain embodiments, the total weight per weight of chromophore or combination of chromophores may be in the amount of about 0.005-1%, 0.05-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40.001% per weight of the silicone-based biophotonic composition of the surfactant phase.

The concentration of the chromophore to be used can be selected based on the desired intensity and duration of the biophotonic activity from the silicone-based biophotonic composition, and on the desired medical or cosmetic effect. For example, some dyes such as xanthene dyes reach a 'saturation concentration' after which further increases in concentration do not provide substantially higher emitted fluorescence. Further increasing the chromophore concentration above the saturation concentration can reduce the amount of activating light passing through the matrix. Therefore, if more fluorescence is required for a certain application than activating light, a high concentration of chromophore can be used. However, if a balance is required between the emitted fluorescence and the activating light, a concentration close to or lower than the saturation concentration can be chosen.

Suitable chromophores that may be used in the silicone-based biophotonic compositions of the present disclosure include, but are not limited to the following:

Chlorophyll Dyes

Exemplary chlorophyll dyes include but are not limited to chlorophyll a; chlorophyll b; chlorophyllin; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Xanthene Derivatives Exemplary xanthene dyes include, but are not limited to, esosin B, eosin B (4',5'-dibromo,2',7'-dinitr-o-fluorescein, dianion); Eosin Y; eosin Y (2',4',5',7'-tetrabromo-fluorescein, dianion); eosin (2',4',5',7'-tetrabromo-fluorescein, dianion); eosin (2',4',5',7'-tetrabromo-fluorescein, dianion) methyl ester; eosin (2',4',5',7'-tetrabromo-fluorescein, monoanion) p-isopropylbenzyl ester; eosin derivative (2',7'-dibromo-fluorescein, dianion); eosin derivative (4',5'-dibromo-fluorescein, dianion); eosin derivative (2',7'-dichloro-fluorescein, dianion); eosin derivative (4',5'-dichloro-fluorescein, dianion); eosin derivative (2',7'-diiodo-fluorescein, dianion); eosin derivative (4',5'-diiodo-fluorescein, dianion); eosin derivative (tribromo-fluorescein, dianion); eosin derivative (2',4',5',7'-tetrachloro-fluorescein, dianion); eosin; eosin dicetylpyridinium chloride ion pair; erythrosin B (2',4',5',7'-tetraiodo-fluorescein, dianion); erythrosin; erythrosin dianion; erythiosin B; fluorescein; fluorescein dianion; phloxin B (2',4',5',7'-tetrabromo-3,4,5,6-tetrachloro-fluorescein, dianion); phloxin B (tetrachloro-tetrabromo-fluorescein); phloxine B; rose bengal (3,4,5,6-tetrachloro-2',4',5',7'-tetraiodofluorescein, dianion); pyronin G, pyronin J, pyronin Y; Rhodamine dyes such as rhodamines include 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Methylene Blue Dyes

Exemplary methylene blue derivatives include but are not limited to 1-methyl methylene blue; 1,9-dimethyl methylene blue; methylene blue; methylene violet; bromomethylene violet; 4-iodomethylene violet; 1,9-dimethyl-3-dimethyl-amino-7-diethyl-amino-phenothiazine; and 1,9-dimethyl-3-diethylamino-7-dibutyl-amino-phenot-hiazine.

Azo Dyes

Exemplary azo (or diazo-) dyes include but are not limited to methyl violet, neutral red, para red (pigment red 1), amaranth (Azorubine S), Carmoisine (azorubine, food red 3, acid red 14), allura red AC (FD&C 40), tartrazine (FD&C Yellow 5), orange G (acid orange 10), Ponceau 4R (food red 7), methyl red (acid red 2), and murexide-ammonium purpurate.

In some aspects of the disclosure, the one or more chromophores of the silicone-based biophotonic compositions disclosed herein can be independently selected from any of Acid black 1, Acid blue 22, Acid blue 93, Acid fuchsin, Acid green, Acid green 1, Acid green 5, Acid magenta, Acid orange 10, Acid red 26, Acid red 29, Acid red 44, Acid red 51, Acid red 66, Acid red 87, Acid red 91, Acid red 92, Acid red 94, Acid red 101, Acid red 103, Acid roseine, Acid rubin, Acid violet 19, Acid yellow 1, Acid yellow 9, Acid yellow 23, Acid yellow 24, Acid yellow 36, Acid yellow 73, Acid yellow S, Acridine orange, Acriflavine, Alcian blue, Alcian yellow, Alcohol soluble eosin, Alizarin, Alizarin blue 2RC, Alizarin carmine, Alizarin cyanin BBS, Alizarol cyanin R, Alizarin red S, Alizarin purpurin, Aluminon, Amido black 10B, Amidoschwarz, Aniline blue WS, Anthracene blue SWR, Auramine O, Azocannine B, Azocarmine G, Azoic diazo 5, Azoic diazo 48, Azure A, Azure B, Azure C, Basic blue 8, Basic blue 9, Basic blue 12, Basic blue 15, Basic blue 17, Basic blue 20, Basic blue 26, Basic brown 1, Basic fuchsin, Basic green 4, Basic orange 14, Basic red 2, Basic red 5, Basic red 9, Basic violet 2, Basic violet 3, Basic violet 4, Basic violet 10, Basic violet 14, Basic yellow 1, Basic yellow 2, Biebrich scarlet, Bismarck brown Y, Brilliant crystal scarlet 6R, Calcium red, Carmine, Carminic acid, Celestine blue B, China blue, Cochineal, Coelestine blue, Chrome violet CG, Chromotrope 2R, Chromoxane cyanin R, Congo corinth, Congo red, Cotton blue, Cotton red, Croceine scarlet, Crocin, Crystal ponceau 6R, Crystal violet, Dahlia, Diamond green B, Direct blue 14, Direct blue 58, Direct red, Direct red 10, Direct red 28, Direct red 80, Direct yellow 7, Eosin B, Eosin Bluish, Eosin, Eosin Y, Eosin yellowish, Eosinol, Erie garnet B, Eriochrome cyanin R, Erythrosin B, Ethyl eosin, Ethyl green, Ethyl violet, Evans blue, Fast blue B, Fast green FCF, Fast red B, Fast yellow, Fluorescein, Food green 3, Gallein, Gallamine blue, Gallocyanin, Gentian violet, Haematein, Haematine, Haematoxylin, Helio fast rubin BBL, Helvetia blue, Hematein, Hematine, Hematoxylin, Hoffman's violet, Imperial red, Indocyanin Green, Ingrain blue, Ingrain blue 1, Ingrain yellow 1, INT, Kermes, Kermesic acid, Kernechtrot, Lac, Laccaic acid, Lauth's violet, Light green, Lissamine green SF, Luxol fast blue, Magenta O, Magenta I, Magenta II, Magenta III, Malachite green, Manchester brown, Martius yellow, Merbromin, Mercurochrome, Metanil yellow, Methylene azure A, Methylene azure B, Methylene azure C, Methylene blue, Methyl blue, Methyl green, Methyl violet, Methyl violet 2B, Methyl violet 10B, Mordant blue 3, Mordant blue 10, Mordant blue 14, Mordant blue 23, Mordant blue 32, Mordant blue 45, Mordant red 3, Mordant red 11, Mordant violet 25, Mordant violet 39 Naphthol blue black, Naphthol green B, Naphthol yellow S, Natural black 1, Natural green 3(chlorophyllin), Natural red, Natural red 3, Natural red 4, Natural red 8, Natural red 16, Natural red 25, Natural red 28, Natural yellow 6, NBT, Neutral red, New fuchsin, Niagara blue 3B, Night blue, Nitro BT, Nitro blue tetrazolium, Nuclear fast red, Orange G, Orcein, Pararosanilin, Phloxine B, Picric acid, Ponceau 2R, Ponceau 6R, Ponceau B, Ponceau de Xylidine, Ponceau S, *Primula*, Purpurin, Pyronin B, phycobilins, Phycocyanins, Phycoerythrins. Phycoerythrincyanin (PEC), Phthalocyanines, Pyronin G, Pyronin Y, Quinine, Rhodamine B, Rosanilin, Rose bengal, Saffron, Safranin O, Scarlet R, Scarlet red, Scharlach R, Shellac, Sirius red F3B, Solochrome cyanin R, Soluble blue, Spirit soluble eosin, Sulfur yellow S, Swiss blue, Tartrazine, Thioflavine S, Thioflavine T, Thionin, Toluidine blue, Toluyline red, Tropaeolin G, Trypaflavine, Trypan blue, Uranin, Victoria blue 4R, Victoria blue B, Victoria green B, Vitamin B, Water blue I, Water soluble eosin, Xylidine ponceau, or Yellowish eosin.

In certain embodiments, the silicone-based biophotonic compositions of the present disclosure includes any of the chromophores listed above, or a combination thereof, so as to provide a synergistic biophotonic effect at the application site.

Without being bound to any particular theory, a synergistic effect of the chromophore combinations means that the biophotonic effect is greater than the sum of their individual effects. Advantageously, this may translate to increased reactivity of the biophotonic composition, faster or improved treatment time. Also, the treatment conditions need not be altered to achieve the same or better treatment results, such as time of exposure to light, power of light source used, and wavelength of light used. In other words, use of synergistic combinations of chromophores may allow the same or better treatment without necessitating a longer time of exposure to a light source, a higher power light source or a light source with different wavelengths.

In some embodiments, the composition includes Eosin Y as a first chromophore and any one or more of Rose Bengal, Fluorescein, Erythrosine, Phloxine B, chlorophyll as a second chromophore. It is believed that these combinations have a synergistic effect as they can transfer energy to one another when activated due in part to overlaps or close proximity of their absorption and emission spectra. This transferred energy is then emitted as fluorescence and/or leads to production of reactive oxygen species. This absorbed and re-emitted light is thought to be transmitted throughout the composition, and also to be transmitted into the site of treatment.

In further embodiments, the silicone-based biophotonic composition may include, for example, the following synergistic combinations: Eosin Y and Fluorescein; Fluorescein and Rose Bengal; Erythrosine in combination with Eosin Y, Rose Bengal or Fluorescein; Phloxine B in combination with one or more of Eosin Y, Rose Bengal, Fluorescein and Erythrosine.

By means of synergistic effects of the chromophore combinations in the silicone-based biophotonic composition, chromophores which cannot normally be activated by an activating light (such as a blue light from an LED), can be activated through energy transfer from chromophores which are activated by the activating light. In this way, the different properties of photoactivated chromophores can be harnessed and tailored according to the cosmetic or the medical therapy required.

For example, Rose Bengal can generate a high yield of singlet oxygen when activated in the presence of molecular oxygen, however it has a low quantum yield in terms of emitted fluorescent light. Rose Bengal has a peak absorption around 540 nm and so can be activated by green light. Eosin Y has a high quantum yield and can be activated by blue light. By combining Rose Bengal with Eosin Y, one obtains a composition which can emit therapeutic fluorescent light and generate singlet oxygen when activated by blue light. In this case, the blue light photoactivates Eosin Y, which transfers some of its energy to Rose Bengal as well as emitting some energy as fluorescence.

In some embodiments, the chromophore or chromophores are selected such that their emitted fluorescent light, on photoactivation, is within one or more of the green, yellow, orange, red and infrared portions of the electromagnetic spectrum, for example having a peak wavelength within the range of about 490 nm to about 800 nm. In certain embodiments, the emitted fluorescent light has a power density of between 0.005 to about 10 mW/cm$^2$, about 0.5 to about 5 mW/cm$^2$.

(b) Surfactant Phase

The silicone-based biophotonic compositions of the present disclosure comprise a surfactant phase. The surfactant may be present in an amount of at least 5%, 10%, 15%, 20%, 25%, or 30% of the total composition. In certain embodiments, the surfactant phase comprises a block copolymer. The term "block copolymer" as used herein refers to a copolymer comprised of 2 or more blocks (or segments) of different homopolymers. The term homopolymer refers to a polymer comprised of a single monomer. Many variations of block copolymers are possible including simple diblock polymers with an A-B architecture and triblock polymers with A-B-A, B-A-B or A-B-C architectures and more complicated block copolymers are known. In addition, unless otherwise indicated herein, the repetition number and type of the monomers or repeating units constituting the block copolymer are not particularly limited. For example, when one denotes the monomeric repeating units as "a" and "b", it is meant herein that this copolymer includes not only a random copolymer having the average composition of $(a)_m(b)_n$, but also a diblock copolymer of the composition $(a)_m(b)_n$, and a triblock copolymer of the composition $(a)_l(b)_m(a)_n$, or the like. In the formulae above, l, m, and n represent the number of repeating units and are positive numbers.

In certain embodiments of any of the foregoing or following the block copolymer is biocompatible. A polymer is "biocompatible" in that the polymer and degradation products thereof are substantially non-toxic to cells or organisms, including non-carcinogenic and non-immunogenic, and are cleared or otherwise degraded in a biological system, such as an organism (patient) without substantial toxic effect.

In certain embodiments the block copolymer of the surfactant phase is from a group of tri-block copolymers designated Poloxamers. Poloxamers are A-B-A block copolymers in which the A segment is a hydrophilic polyethylene glycol (PEG) homopolymer and the B segment is hydrophobic polypropylene glycol (PPG) homopolymer. PEG is also known as polyethylene oxide (PEO) or polyoxyethylene (POE), depending on its molecular weight. Additionally, PPG is also known as polypropylene oxide (PPO), depending on its molecular weight. Poloxamers are commercially available from BASF Corporation. Poloxamers produce reverse thermal gelatin compositions, i.e., with the characteristic that their viscosity increases with increasing temperature up to a point from which viscosity again decreases. Depending on the relative size of the blocks the copolymer can be a solid, liquid or paste. In certain embodiments of the disclosure, the poloxamer is Pluronic® F127 (also known as Poloxamer 407). In some embodiments of the silicone-based biophotonic composition may comprise Pluronic® F127 in the amount of 1-40 wt % of the total composition. In some embodiments of the silicone-based biophotonic composition may comprise 1-5 wt %, 2.5-7.5 wt %, 5-10 wt %, 7.5-12.5 wt %, 10-15 wt %, 12.5-17.5 wt %, 15-20 wt %, 20-25 wt %, 25-30 wt %, 30-35 wt %, 35-40 wt % pluronic. In certain embodiments Pluronic® F127 is present in the amount of 2-8 wt % of the total composition of the silicone-based biophotonic composition.

In certain embodiments of the disclosure the surfactant phase comprises a block copolymer comprising at least an A-B unit, wherein A is PEG and B is polylactic acid (PLA), or polyglycolic acid (PGA) or poly(lactic-co-glycolic acid) (PLGA) or polycaprolactone (PCL) or polydioxanone (PDO).

Since the PEG blocks contribute hydrophilicity to the polymer, increasing the length of the PEG blocks or the total amount of PEG in the polymer will tend to make the polymer more hydrophilic. Depending on the amounts and proportions of the other components of the polymer, the desired overall hydrophilicity, and the nature and chemical functional groups of any chromophore that may be included in a formulation of the polymer, a skilled person can readily adjust the length (or MW) of the PEG blocks used and/or the total amount of PEG incorporated into the polymer, in order to obtain a polymer having the desired physical and chemical characteristics.

The total amount of PEG in the polymer may be about 80 wt % or less, 75 wt % or less, 70 wt % or less, 65 wt % or less, about 60 wt % or less, about 55 wt % or less, or about 50 wt % or less. In particular embodiments, the total amount of PEG is about 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, or about 70 wt %. Unless otherwise specified, a weight percentage of a particular component of the polymer means that the total weight of the polymer is made up of the specified percentage of monomers of that component. For example, 65 wt % PEG means that 65% of the weight of the polymer is made up of PEG monomers, which monomers are linked into blocks of varying lengths, which blocks are distributed along the length of polymer, including in a random distribution.

The total amount of PPG or PLA or PLGA or PCL or PDO present in the block copolymer may be about 50 wt % or less, about 45 wt % or less, about 40 wt % or less, about 35 wt % or less, about 30 wt % or less, about 25 wt % or less, or about 20 wt % or less.

The surfactant phase may also include thickening agents or stabilizers such as gelatin and/or modified celluloses such as hydroxyethyl cellulose (HEC) and carboxymethyl cellulose (CMD), and/or polysaccharides such as xanthan gum, guar gum, and/or starches and/or any other thickening agent. In certain embodiments of the disclosure, the stabilizer or thickening agent may comprise gelatin. For example, the surfactant phase may comprise about 0-5 wt %, about 5-25 wt %, about 0-15 wt %, or about 10-20 wt % gelatin.

Surfactants and/or stabilizers may be selected according to effects they will have on the optical transparency of the biophotonic membrane. The silicone-based biophotonic composition should be able to transmit sufficient light to activate the at least one chromophore and, in embodiments where fluorescence is emitted by the activated chromophore, the surfactant phase should also be able to transmit the emitted fluorescent light to tissues.

(c) Silicone Phase

The silicone-based biophotonic compositions of the present disclosure comprise a continuous phase of silicone. Silicones are synthetic polymers containing chains consisting of (—Si—O—) repeating unit with two organic groups attached directly to the Si atom. In certain embodiments, the silicone is a polydimethylsiloxane (PDMS) fluid $(Me_2SiO)_n$ or a PDMS-based gel or PDMS-based elastomer.

Non-limiting examples of PDMS polymers include those sold under the trademark Sylgard, and particularly Sylgard 182, Sylgard 184, Sylgard 186 and Sylgard 527. In certain embodiments, the silicone phase of the silicone-based biophotonic composition can be prepared by using commercial kits such as Sylgard® 184 Silicone Elastomer kit. The kit consists in two-part liquid components, the base (part A) and the curing agent or catalyst (part B), both based on polydimethylsiloxane. When mixed at a ratio of 10(A)/1(B), the mixture cures to a flexible and transparent elastomer.

Sylgard 184 is a silicone elastomer comprising a polydimethyl siloxane and an organically-modified silica. Sylgard 184 is prepared by combining a base (Part A) with a curing agent (Part B). The base contains about >60 wt % dimethylvinyl-terminated dimethyl siloxane, about 30 to 60 wt % dimethylvinylated and trimethylated silica and about 1 to 5 wt % tetra(trimethylsiloxy) silane. The curing agent contains about 40 to 70 wt % dimethyl, methylhydrogen siloxane, about 15 to 40 wt % dimethylvinyl-terminated dimethyl siloxane, about 10 to 30 wt % dimethylvinylated and trimethylated silica and about 1 to 5 wt % tetramethyl tetravinyl cyclotetrasiloxane.

In another embodiment, the silicone phase of the silicone-based biophotonic composition can be prepared by using the Sylgard® 527 Silicone Gel kit, which allows the preparation of a soft and sticky gel, when the two parts A and B are mixed at the ratio 1(A)/1(B). Parts A and B of Sylgard contain about 85 to 100 wt % dimethylvinyl-terminated dimethyl siloxane and about 1 to 5 wt % dimethyl, methylhydrogen siloxane.

In other embodiments, the silicone-based biophotonic composition may be prepared in a manner to provide for tunable flexibility were desired, for example a silicone-based biophotonic membrane having tunable flexibility. One means of generating a tunable silicone-based biophotonic membrane of the present disclosure is by combining different ratios of commercially available PDMS such as Sylgard® 184 and Sylgard® 527. In some embodiments the silicone phase comprises Sylgard® 184 in the amount of 5-100 wt % of the silicone phase. In certain embodiments of the present disclosure the Sylgard® 184 is present in an amount of about 5-10 wt %, 10-15 wt %, 15-20 wt %, 20-25 wt %, 25-30 wt %, 30-35 wt %, 35-40 wt %, 40-45 wt %, 45-50 wt %, 50-55 wt %, 55-60 wt %, 60-65 wt % 65-70 wt %, 70-75 wt %, 75-80 wt %, 80-85 wt %, 85-90 wt %, 90-95 wt % or 95-100 wt % of the silicone phase. In certain embodiments of the present disclosure, the silicone phase comprises Sylgard® 527. In certain other embodiments of the present disclosure, the Sylgard® 527 is present in an amount of about 5-10 wt %, 10-15 wt %, 15-20 wt %, 20-25 wt %, 25-30 wt %, 30-35 wt %, 35-40 wt %, 40-45 wt %, 45-50 wt %, 50-55 wt %, 55-60 wt %, 60-65 wt % 65-70 wt %, 70-75 wt %, 75-80 wt %, 80-85 wt %, 85-90 wt %, 90-95 wt % or 95-100 wt % of the silicone phase.

In one embodiment, the silicone phase of the silicone-based biophotonic composition is a mixture using 15% Sylgard 184 and 85% Sylgard 527.

(d) Oxidizing Agents and Antimicrobials

According to certain embodiments, the silicone-based biophotonic composition of the present disclosure, or the surfactant phase of these silicone-based biophotonic compositions, may optionally comprise one or more additional components, such as oxygen-rich compounds as a source of oxygen radicals. The oxygen-rich compounds include but are not limited to peroxides, such as hydrogen peroxide, benzoyl peroxide and urea peroxide. Peroxide compounds are oxidants that contain the peroxy group (R—O—O—R), which is a chainlike structure containing two oxygen atoms, each of which is bonded to the other and a radical or some element. When a silicone-based biophotonic composition of the present disclosure is illuminated with light, the chromophores are excited to a higher energy state. When the chromophores' electrons return to a lower energy state, they emit photons with a lower energy level, thus causing the emission of light of a longer wavelength (Stokes' shift). Some of this energy may be transferred to the oxidizing agent and may cause the formation of oxygen radicals, such as singlet oxygen. These oxygen radicals may contribute to the degradation of the chromophore.

Hydrogen peroxide ($H_2O_2$) is a powerful oxidizing agent, and breaks down into water and oxygen and does not form any persistent, toxic residual compound. A suitable range of concentration over which hydrogen peroxide can be used in the silicone-based biophotonic composition is from about 0.1% to about 3%, about 0.1 to 1.5%, about 0.1% to about 1%, about 1%, less than about 1%.

Urea hydrogen peroxide (also known as urea peroxide, carbamide peroxide or percarbamide) is soluble in water and contains approximately 35% hydrogen peroxide. A suitable range of concentration over which urea peroxide can be used in the silicone-based biophotonic composition of the present disclosure is less than about 0.25%, or less than about 0.3%, from 0.001 to 0.25%, or from about 0.3% to about 5%. Urea peroxide breaks down to urea and hydrogen peroxide in a slow-release fashion that can be accelerated with heat or photochemical reactions.

Benzoyl peroxide consists of two benzoyl groups (benzoic acid with the H of the carboxylic acid removed) joined by a peroxide group. A suitable range of concentration over which benzoyl peroxide can be used in the silicone-based biophotonic composition is from about 2.5% to about 5%.

Antimicrobials kill microbes or inhibit their growth or accumulation, and may optionally be included with the silicone-based biophotonic compositions of the present disclosure. Suitable antimicrobials for use in the methods and compositions of the present disclosure include, but not limited to, hydrogen peroxide, urea hydrogen peroxide, benzoyl peroxide, phenolic and chlorinated phenolic and chlorinated phenolic compounds, resorcinol and its derivatives, bisphenolic compounds, benzoic esters (parabens), halogenated carbonilides, polymeric antimicrobial agents, thazolines, trichloromethylthioimides, natural antimicrobial agents (also referred to as "natural essential oils"), metal salts, and broad-spectrum antibiotics.

Specific phenolic and chlorinated phenolic antimicrobial agents that can be used in the disclosure include, but are not limited to: phenol; 2-methyl phenol; 3-methyl phenol; 4-methyl phenol; 4-ethyl phenol; 2,4-dimethyl phenol; 2,5-dimethyl phenol; 3,4-dimethyl phenol; 2,6-dimethyl phenol; 4-n-propyl phenol; 4-n-butyl phenol; 4-n-amyl phenol; 4-tert-amyl phenol; 4-n-hexyl phenol; 4-n-heptyl phenol; mono- and poly-alkyl and aromatic halophenols; p-chlorophenyl; methyl p-chlorophenol; ethyl p-chlorophenol; n-propyl p-chlorophenol; n-butyl p-chlorophenol; n-amyl p-chlorophenol; sec-amyl p-chlorophenol; n-hexyl p-chlorophenol; cyclohexyl p-chlorophenol; n-heptyl p-chlorophenol; n-octyl; p-chlorophenol; o-chlorophenol; methyl o-chlorophenol; ethyl o-chlorophenol; n-propyl o-chlorophenol; n-butyl o-chlorophenol; n-amyl o-chlorophenol; tert-amyl o-chlorophenol; n-hexyl o-chlorophenol; n-heptyl o-chlorophenol; o-benzyl p-chlorophenol; o-benxyl-m-methyl p-chlorophenol; o-benzyl-m,m-dimethyl p-chlorophenol; o-phenylethyl p-chlorophenol; o-phenylethyl-m-methyl p-chlorophenol; 3-methyl p-chlorophenol 3,5- dimethyl p-chlorophenol, 6-ethyl-3-methyl p-chlorophenol, 6-n-propyl-3-methyl p-chlorophenol; 6-iso-propyl-3-methyl p-chlorophenol; 2-ethyl-3,5-dimethyl p-chlorophenol; 6-sec-butyl-3-methyl p-chlorophenol; 2-iso-propyl-3,5-dimethyl p-chlorophenol; 6-diethylmethyl-3-methyl p-chlorophenol; 6-iso-propyl-2-ethyl-3-methyl p-chlorophenol; 2-sec-amyl-3,5-dimethyl p-chlorophenol; 2-diethylmethyl-3,5-dimethyl p-chlorophenol; 6-sec-octyl-3-methyl p-chlorophenol; p-chloro-m-cresol p-bromophenol; methyl p-bromophenol; ethyl p-bromophenol; n-propyl p-bromophenol; n-butyl p-bromophenol; n-amyl p-bromophenol; sec-amyl p-bromophenol; n-hexyl p-bromophenol; cyclohexyl p-bromophenol; o-bromophenol; tert-amyl o-bromophenol; n-hexyl o-bromophenol; n-propyl-m,m-dimethyl o-bromophenol; 2-phenyl phenol; 4-chloro-2-methyl phenol; 4-chloro-3-methyl phenol; 4-chloro-3,5-dimethyl phenol; 2,4-dichloro-3,5-dimethylphenol; 3,4,5,6-tetabromo-2-methylphenol-; 5-methyl-2-pentylphenol; 4-isopropyl-3-methylphenol; para-chloro-metaxylenol (PCMX); chlorothymol; phenoxyethanol; phenoxyisopropanol; and 5-chloro-2-hydroxydiphenylmethane.

Resorcinol and its derivatives can also be used as antimicrobial agents. Specific resorcinol derivatives include, but are not limited to: methyl resorcinol; ethyl resorcinol; n-propyl resorcinol; n-butyl resorcinol; n-amyl resorcinol; n-hexyl resorcinol; n-heptyl resorcinol; n-octyl resorcinol; n-nonyl resorcinol; phenyl resorcinol; benzyl resorcinol; phenylethyl resorcinol; phenylpropyl resorcinol; p-chlorobenzyl resorcinol; 5-chloro-2,4-dihydroxydiphenyl methane; 4'-chloro-2,4-dihydroxydiphenyl methane; 5-bromo-2,4-dihydroxydiphenyl methane; and 4'-bromo-2,4-dihydroxydiphenyl methane.

Specific bisphenolic antimicrobial agents that can be used in the disclosure include, but are not limited to: 2,2'-methylene bis-(4-chlorophenol); 2,4,4'trichloro-2'-hydroxydiphenyl ether, which is sold by Ciba Geigy, Florham Park, N.J. under the tradename Triclosan®; 2,2'-methylene bis-(3,4,6-trichlorophenol); 2,2'-methylene bis-(4-chloro-6-bromophenol); bis-(2-hydroxy-3,5-dichlorop-henyl) sulphide; and bis-(2-hydroxy-5-chlorobenzyl)sulphide.

Specific benzoie esters (parabens) that can be used in the disclosure include, but are not limited to: methylparaben; propylparaben; butylparaben; ethylparaben; isopropylparaben; isobutylparaben; benzylparaben; sodium methylparaben; and sodium propylparaben.

Specific halogenated carbanilides that can be used in the disclosure include, but are not limited to: 3,4,4'-trichlorocarbanilides, such as 3-(4-chlorophenyl)-1-(3,4-dichlorphenyl)urea sold under the tradename Triclocarban® by Ciba-Geigy, Florham Park, N.J.; 3-trifluoromethyl-4,4'-dichlorocarbanilide; and 3,3',4-trichlorocarbanilide Specific polymeric antimicrobial agents that can be used in the disclosure include, but are not limited to: polyhexamethylene biguanide hydrochloride; and poly(iminoimidocarbonyl iminoimidocarbonyl iminohexamethylene hydrochloride), which is sold under the tradename Vantocil® IB.

Specific thazolines that can be used in the disclosure include, but are not limited to that sold under the tradename Micro-Check® and 2-n-octyl-4-isothiazolin-3-one, which is sold under the tradename Vinyzene® IT-3000 DIDP.

Specific trichloromethylthioimides that can be used in the disclosure include, but are not limited to: N-(trichloromethylthio)phthalimide, which is sold under the tradename Fungitrol®; and N-trichloromethylthio-4-cyclohexene-1,2-dicarboximide, which is sold under the tradename Vancide®.

Specific natural antimicrobial agents that can be used in the disclosure include, but are not limited to, oils of: anise; lemon; orange; rosemary; wintergreen; thyme; lavender; cloves; hops; tea tree; citronella; wheat; barley; lemongrass; cedar leaf; cedarwood; cinnamon; fleagrass; geranium; sandalwood; violet; cranberry; *eucalyptus*; vervain; peppermint; gum benzoin; basil; fennel; fir; balsam; menthol; ocmea origanuin; hydastis; carradensis; Berberidaceac daceae; Ratanhiae *longa*; and *Curcuma longa*. Also included in this class of natural antimicrobial agents are the key chemical components of the plant oils which have been found to provide antimicrobial benefit. These chemicals include, but are not limited to: anethol; catechole; camphene; thymol; eugenol; eucalyptol; ferulic acid; farnesol; hinokitiol; tropolone; limonene; menthol; methyl salicylate; carvacol; terpineol; verbenone; berberine; ratanhiae extract; caryophellene oxide; citronellic acid; curcumin; nerolidol; and geraniol.

Specific metal salts that can be used in the disclosure include, but are not limited to, salts of metals in groups 3a-5a, 3b-7b, and 8 of the periodic table. Specific examples of metal salts include, but are not limited to, salts of: aluminum; zirconium; zinc; silver; gold; copper; lanthanum; tin; mercury; bismuth; selenium; strontium; scandium; yttrium; cerium; praseodymiun; neodymium; promethum; samarium; europium; gadolinium; terbium; dysprosium; holmium; erbium; thalium; ytterbium; lutetium; and mixtures thereof. An example of the metal-ion based antimicrobial agent is sold under the tradename HealthShield®, and is manufactured by HealthShield Technology, Wakefield, Mass.

Specific broad-spectrum antimicrobial agents that can be used in the disclosure include, but are not limited to, those that are recited in other categories of antimicrobial agents herein.

Additional antimicrobial agents that can be used in the methods of the disclosure include, but are not limited to: pyrithiones, and in particular pyrithione-including zinc complexes such as that sold under the tradename Octopirox®; dimethyidimethylol hydantoin, which is sold under the tradename Glydant®; methylchloroisothiazolinone/methylisothiazolinone, which is sold under the tradename Kathon CG®; sodium sulfite; sodium bisulfite; imidazolidinyl urea, which is sold under the tradename Germall 115®; diazolidinyl urea, which is sold under the tradename Germall 110; benzyl alcohol v2-bromo-2-nitropropane-1,3-diol, which is sold under the tradename Bronopol®; formalin or formaldehyde; iodopropenyl butylcarbamate, which is sold under the tradename Polyphase P100®; chloroacetamide; methanamine; methyldibromonitrile glutaronitrile (1,2-dibromo-2,4-dicyanobutane), which is sold under the tradename Tektamer®; glutaraldehyde; 5-bromo-5-nitro-1,3-dioxane, which is sold under the tradename Bronidox®; phenethyl alcohol; o-phenylphenol/sodium o-phenylphenol sodium hydroxymethylglycinate, which is sold under the tradename Suttocide A®; polymethoxy bicyclic oxazolidine; which is sold under the tradename Nuosept C®; dimethoxane; thimersal; dichlorobenzyl alcohol; captan; chlorphenenesin; dichlorophene; chlorbutanol; glyceryl laurate; halogenated diphenyl ethers; 2,4,4'-trichloro-2'-hydroxy-diphenyl ether, which is sold under the tradename Triclosan® and is available from Ciba-Geigy, Florham Park, N.J.; and 2,2'-dihydroxy-5,5'-dibromo-diphenyl ether.

(4) Optical Properties of the Silicone-Based Biophotonic Compositions

In certain embodiments, silicone-based biophotonic compositions of the present disclosure are substantially transparent or translucent. The % transmittance of the silicone-based biophotonic composition can be measured in the range of wavelengths from 250 nm to 800 nm using, for example, a Perkin-Elmer Lambda 9500 series UV-visible spectrophotometer. In some embodiments, transmittance within the visible range is measured and averaged. In some other embodiments, transmittance of the silicone-based biophotonic composition is measured with the chromophore omitted. As transmittance is dependent upon thickness, the thickness of each sample can be measured with calipers prior to loading in the spectrophotometer. Transmittance values can be normalized according to $$F_{T-corr}(\lambda, t_2) = [e^{-\sigma_t(\lambda)t_1}]^{\frac{t_2}{t_1}} = [F_{T-corr}(\lambda, t_1)]^{\frac{t_2}{t_1}},$$

where $t_1$=actual specimen thickness, $t_2$=thickness to which transmittance measurements can be normalized. In the art, transmittance measurements are usually normalized to 1 cm.

In some embodiments, the silicone-based biophotonic composition has a transmittance that is more than about 20%, 30%, 40%, 50%, 60%, 70%, or 75% within the visible range. In some embodiments, the transmittance exceeds 40%, 41%, 42%, 43%, 44%, or 45% within the visible range. In some embodiments, the silicone-based biophotonic composition has a light transmittance of about 40-100%, 45-100%, 50-100%, 55-100%, 60-100%, 65-100%, 70-100%, 75-100%, 80-100%, 85-100%, 90-100%, or 95-100%.

(5) Forms of the Silicone-Based Biophotonic Compositions

The silicone-based biophotonic compositions of the present disclosure may be in the form of a silicone-based biophotonic membrane containing at least one chromophore.

The silicone-based biophotonic membranes of the present disclosure may be deformable. They may be elastic or non-elastic (i.e. flexible or rigid). The silicone-based biophotonic membrane, for example, may be in a peel-off form ('peelable') to provide ease and speed of use. In certain embodiments, the tear strength and/or tensile strength of the peel-off form is greater than its adhesion strength. This may help handleability of the silicone-based biophotonic membrane. It will be recognized by one of skill in the art that the properties of the peel-off silicone-based biophotonic membrane such as cohesiveness, flexibility, elasticity, tensile strength, and tearing strength, can be determined and/or adjusted by methods known in the art such as by selecting suitable PDMS-based compositions and adapting their relative ratios.

The silicone-based biophotonic composition may be provided in a pre-formed shape. In certain embodiments, the pre-formed shape is in the form of, including, but not limited to, a film, a face mask, a patch, a dressing, or bandage. In certain embodiments, the pre-formed shapes can be customized for the individual user by trimming to size. In certain embodiments, perforations are provided around the perimeter of the pre-formed shape to facilitate trimming. In certain embodiments, the pre-shaping can be performed manually or by mechanical means such as 3-D printing. In the case of the 3-D printing the size of the area to be treated can be imaged, such as a wound or a face, then a 3-D printer configured to build or form a cohesive silicone-based biophotonic composition to match the size and shape of the imaged treatment area.

A silicone-based biophotonic composition of the disclosure can be configured with a shape and/or size for application to a desired portion of a subject's body. For example, the silicone-based biophotonic composition can be shaped and sized to correspond with a desired portion of the body to receive the biophotonic treatment. Such a desired portion of skin can be selected from, but not limited to, the group consisting of a skin, head, forehead, scalp, nose, cheeks, lips, ears, face, neck, shoulder, arm pit, arm, elbow, hand, finger, abdomen, chest, stomach, back, buttocks, sacrum, genitals, legs, knee, feet, toes, nails, hair, any boney prominences, and combinations thereof, and the like. Thus, the silicone-based biophotonic composition of the disclosure can be shaped and sized to be applied to any portion of skin on a subject's body. For example, the silicone-based biophotonic composition can be in the form of a sock, hat, glove or mitten shaped form. In embodiments where the silicone-based biophotonic composition is in a elastic, semi-rigid or rigid form, it may be peeled-off without leaving any residue on the tissue.

In certain embodiments, the silicone-based biophotonic composition is provided in the form of an elastic and peelable face mask, which may be pre-formed. In other embodiments, the silicone-based biophotonic composition is in the form of a non-elastic (rigid) face mask, which may also be pre-formed. The mask can have openings for one or more of the eyes, nose and mouth. In a further embodiment, the openings are protected with a covering, or the exposed skin such as on the nose, lips or eyes are protected using for example cocoa butter. In certain embodiments, the pre-formed face mask is provided in the form of multiple parts, e.g., an upper face part and a lower face part. In certain embodiments, the uneven proximity of the face to a light source is compensated for, e.g., by adjusting the thickness of the mask, or by adjusting the amount of chromophore in the different areas of the mask, or by blocking the skin in closest proximity to the light. In certain embodiments, the pre-formed shapes come in a one-size fits all form.

In certain embodiments, the silicone-based biophotonic composition is in the form of a wound dressing or a bandage. It may be used on a wound to prevent or limit scar formation, or on an existing scar to diminish the appearance of the scar.

In certain aspects, the mask (or patch) is not pre-formed and is applied e.g., by spreading a silicone-based biophotonic composition making up the mask (or patch), on the skin or target tissue, or alternatively by smearing, dabbing or rolling the composition on target tissue. It can then be converted to a peel-off form after application, by means such as, but not limited to, drying or inducing a change in temperature upon application to the skin or tissue. After use, the mask (or patch) can then be peeled off without leaving any flakes on the skin or tissue, preferably without wiping or washing.

The silicone-based biophotonic compositions of the present disclosure may, for example when provided in the form of a silicone-based biophotonic membrane, mask or dressing, have a thickness of from about 0.1 mm to about 50 mm, about 0.5 mm to about 20 mm, or about 1 mm to about 10 mm. It will be appreciated that the thickness will vary based on the intended use. In some embodiments, the thickness ranges from about 0.1-1 mm. In some embodiments, the thickness ranges from about 0.5-1.5 mm, about 1-2 mm, about 1.5-2.5 mm, about 2-3 mm, about 2.5-3.5 mm, about 3-4 mm, about 3.5-4.5 mm, about 4-5 mm, about 4.5-5.5 mm, about 5-6 mm, about 5.5-6.5 mm, about 6-7 mm, about 6.5-7.5 mm, about 7-8 mm, about 7.5-8.5 mm, about 8-9 mm, about 8.5-9.5, about 9-10 mm, about 10-11 mm, about 11-12 mm, about 12-13 mm, about 13-14 mm, about 14-15 mm, about 15-16 mm, about 16-17 mm, about 17-18 mm, about 18-19 mm, about 19-20 mm, about 20-22 mm, about 22-24 mm, about 24-26 mm, about 26-28 mm, about 28-30 mm, about 30-35 mm, about 35-40 mm, about 40-45 mm, about 45-50 mm.

The tensile strength of the silicone-based biophotonic compositions will vary based on the intended use. The tensile strength can be determined by performing a tensile test and recording the force and displacement. These are then converted to stress (using cross sectional area) and strain; the highest point of the stress-strain curve is the "ultimate tensile strength." In some embodiments, for example when in the form of a silicone-based biophotonic membrane, tensile strength can be characterized using a 500N capacity tabletop mechanical testing system (#5942R4910, Instron®) with a 5N maximum static load cell (#102608, Instron). Pneumatic side action grips can be used to secure the samples (#2712-019, Instron). In some embodiments, a constant extension rate (for example, of about 2 mm/min) until failure can be applied and the tensile strength is calculated from the stress vs. strain data plots. In some embodiments, the tensile strength can be measured using methods as described in or equivalent to those described in American Society for Testing and Materials tensile testing methods such as ASTM D638, ASTM D882 and ASTM D412.

In some embodiments, the silicone-based biophotonic composition has a tensile strength that is at least about 50 kPa, at least about 100 kPa, at least about 200 kPa, at least about 300 kPa, at least about 400 kPa, at least about 500 kPa, at least about 600 kPa, at least about 700 kPa, at least about 800 kPa, at least about 900 kPa, at least about 1 MPa, at least about 2 MPa or at least about 3 MPa, or at least about 5 MPa, or at least about 6 MPa. In some embodiments, the tensile strength of the silicone-based biophotonic composition is up to about 10 MPa.

The tear strength of the silicone-based biophotonic composition will vary depending on the intended use. The tear strength property of the silicone-based biophotonic composition, for example when provided in the form of a silicone-based biophotonic membrane, can be tested using a 500N capacity tabletop mechanical testing system (#5942R4910, Instron) with a 5N maximum static load cell (#102608, Instron). Pneumatic side action grips can be used to secure the samples (#2712-019, Instron). Samples can be tested with a constant extension rate (for example, of about 2 mm/min) until failure. In accordance with the invention, tear strength is calculated as the force at failure divided by the average thickness (N/mm).

In some embodiments, the silicone-based biophotonic composition has a tear strength of from about 0.1 N/mm to about 5 N/mm. In some embodiments, the tear strength is from about 0.1 N/mm to about 0.5 N/mm, from about 0.25 N/mm to about 0.75 N/mm, from about 0.5 N/mm to about 1.0 N/mm, from about 0.75 N/mm to about 1.25 N/mm, from about 1.0 N/mm to about 1.5 N/mm, from about 1.5 N/mm to about 2.0 N/mm, from about 2.0 N/mm to about 2.5 N/mm, from about 2.5 N/mm to about 3.0 N/mm, from about 3.0 N/mm to about 3.5 N/mm, from about 3.5 N/mm to about 4.0 N/mm, from about 4.0 N/mm to about 4.5 N/mm, from about 4.5 N/mm to about 5.0 N/mm.

The adhesion strength of the silicone-based biophotonic composition will vary depending on the intended use. Adhesion strength can be determined in accordance with ASTM D-3330-78, PSTC-101 and is a measure of the force required to remove a silicone-based biophotonic composition from a test panel at a specific angle and rate of removal. In some embodiments, a predetermined size of the silicone-based biophotonic composition, for example a silicone-based biophotonic membrane, is applied to a horizontal surface of a clean glass test plate. A hard rubber roller is used to firmly apply a piece of the silicone-based biophotonic membrane and remove all discontinuities and entrapped air. The free end of the piece of silicone-based biophotonic membrane is then doubled back nearly touching itself so that the angle of removal of the piece from the glass plate will be 180 degrees. The free end of the piece of silicone-based biophotonic membrane is attached to the adhesion tester scale (e.g. an Instron tensile tester or Harvey tensile tester). The test plate is then clamped in the jaws of the tensile testing machine capable of moving the plate away from the scale at a predetermined constant rate. The scale reading in kg is recorded as the silicone-based biophotonic membrane is peeled from the glass surface.

In some embodiments, the adhesion strength can be measured by taking into account the static friction of the silicone-based biophotonic composition. For some embodiments of the silicone-based biophotonic compositions of the present disclosure, the adhesive properties are linked to their levels of static friction, or stiction. In these cases, the adhesion strength can be measured by placing a sample of the silicone-based biophotonic composition such as a silicone-based biophotonic membrane on a test surface and pulling one end of the sample at an angle of approximately 0° (substantially parallel to the surface) whilst applying a known downward force (e.g. a weight) on the sample and measuring the weight at which the sample slips from the surface. The normal force $F_n$, is the force exerted by each surface on the other in a perpendicular (normal) direction to the surface and is calculated by multiplying the combined weight of the sample and the weight by the gravity constant (g) (9.8 m/s$^2$). The sample with the weight on top is then pulled away from a balance until the sample slips from the surface and the weight is recorded on the scale. The weight recorded on the scale is equivalent to the force required to overcome the friction. The force of friction ($F_f$) is then calculated by multiplying the weight recorded on the scale by g. Since $F_f \leq \mu F_n$ (Coulomb's friction law), the friction coefficient $\mu$ can be obtained by dividing $F_f/F_n$. The stress required to shear a material from a surface (adhesion strength) can then be calculated from the friction coefficient, $\mu$, by multiplying the weight of the material by the friction coefficient.

In some embodiments, the silicone-based biophotonic composition has an adhesion strength that is less than its tensile strength or its tear strength.

In some embodiments, the silicone-based biophotonic composition has an adhesion strength of from about 0.01 N/mm to about 0.60 N/mm. In some embodiments, the adhesion strength is from about 0.20 N/mm to about 0.40 N/mm, or from about 0.25 N/mm to about 0.35 N/mm. In some embodiments, the adhesion strength is less than about 0.10 N/mm, less than about 0.15 N/mm, less than about 0.20 N/mm, less than about 0.25 N/mm, less than about 0.30 N/mm, less than about 0.35 N/mm, less than about 0.40 N/mm, less than about 0.45 N/mm, less than about 0.55 N/mm or less than about 0.60 N/mm (6) Methods of Use The silicone-based biophotonic compositions of the present disclosure may have cosmetic and/or medical benefits. They may be used to promote skin rejuvenation and skin conditioning, or to promote the treatment of a skin disorder such as acne, eczema, dermatitis or psoriasis, or to promote tissue repair, modulate inflammation, modulate collagen synthesis, reduce or avoid scarring, or promote wound healing including reducing depth of periodontitis pockets. In certain embodiments, the silicone-based biophotonic composition of the disclosure maybe used to treat acute inflammation, which may present itself as pain, heat, redness, swelling and loss of function, and which includes those seen in allergic reactions such as insect bites e.g.; mosquito, bees, wasps, poison ivy, or post-ablative treatment.

Accordingly, in certain embodiments, the present disclosure provides a method for treating acute inflammation.

In certain embodiments, the present disclosure provides a method for providing skin rejuvenation or for improving skin condition, treating a skin disorder, preventing or treating scarring, and/or accelerating wound healing and/or tissue repair, the method comprising: applying a silicone-based biophotonic composition of the present disclosure to the area of the skin or tissue in need of treatment, and illuminating the silicone-based biophotonic composition with light having a wavelength that overlaps with an absorption spectrum of the chromophore(s) present in the composition.

In the methods of the present disclosure, any source of actinic light can be used. Any type of halogen, LED or plasma arc lamp, or laser may be suitable. The primary characteristic of suitable sources of actinic light will be that they emit light in a wavelength (or wavelengths) appropriate for activating the one or more photoactivators present in the composition. In one embodiment, an argon laser is used. In another embodiment, a potassium-titanyl phosphate (KTP) laser (e.g. a GreenLight™ laser) is used. In yet another embodiment, a LED lamp such as a photocuring device is the source of the actinic light. In yet another embodiment, the source of the actinic light is a source of light having a wavelength between about 200 to 800 nm. In another embodiment, the source of the actinic light is a source of visible light having a wavelength between about 400 and 600 nm. In another embodiment, the source of the actinic light is a source of visible light having a wavelength between about 400 and 700 nm. In yet another embodiment, the source of the actinic light is blue light. In yet another embodiment, the source of the actinic light is red light. In yet another embodiment, the source of the actinic light is green light. Furthermore, the source of actinic light should have a suitable power density. Suitable power density for non-collimated light sources (LED, halogen or plasma lamps) are in the range from about 0.1 mW/cm$^2$ to about 200 mW/cm$^2$. Suitable power density for laser light sources are in the range from about 0.5 mW/cm$^2$ to about 0.8 mW/cm$^2$.

In some embodiments of the methods of the present disclosure, the light has an energy at the subject's skin surface of between about 0.1 mW/cm$^2$ and about 500 mW/cm$^2$, or 0.1-300 mW/cm$^2$, or 0.1-200 mW/cm$^2$, wherein the energy applied depends at least on the condition being treated, the wavelength of the light, the distance of the skin from the light source and the thickness of the biophotonic material. In certain embodiments, the light at the subject's skin is between about 1-40 mW/cm$^2$, or 20-60 mW/cm$^2$, or 40-80 mW/cm$^2$, or 60-100 mW/cm$^2$, or 80-120 mW/cm$^2$, or 100-140 mW/cm$^2$, or 30-180 mW/cm$^2$, or 120-160 mW/cm$^2$, or 140-180 mW/cm$^2$, or 160-200 mW/cm$^2$, or 110-240 mW/cm$^2$, or 110-150 mW/cm$^2$, or 190-240 mW/cm$^2$.

The activation of the chromophore(s) within the silicone-based biophotonic composition may take place almost immediately on illumination (femto- or pico seconds). A prolonged exposure period may be beneficial to exploit the synergistic effects of the absorbed, reflected and reemitted light of the silicone-based biophotonic composition of the present disclosure and its interaction with the tissue being treated. In one embodiment, the time of exposure of the tissue or skin or silicone-based biophotonic composition to actinic light is a period between 0.01 minutes and 90 minutes. In another embodiment, the time of exposure of the tissue or skin or silicone-based biophotonic composition to actinic light is a period between 1 minute and 5 minutes. In some other embodiments, the silicone-based biophotonic composition is illuminated for a period between 1 minute and 3 minutes. In certain embodiments, light is applied for a period of 1-30 seconds, 15-45 seconds, 30-60 seconds, 0.75-1.5 minutes, 1-2 minutes, 1.5-2.5 minutes, 2-3 minutes, 2.5-3.5 minutes, 3-4 minutes, 3.5-4.5 minutes, 4-5 minutes, 5-10 minutes, 10-15 minutes, 15-20 minutes, or 20-30 minutes. The treatment time may range up to about 90 minutes, about 80 minutes, about 70 minutes, about 60 minutes, about 50 minutes, about 40 minutes or about 30 minutes. It will be appreciated that the treatment time can be adjusted in order to maintain a dosage by adjusting the rate of fluence delivered to a treatment area. For example, the delivered fluence may be about 4 to about 60 J/cm$^2$, about 10 to about 60 J/cm$^2$, about 10 to about 50 J/cm$^2$, about 10 to about 40 J/cm$^2$, about 10 to about 30 J/cm$^2$, about 20 to about 40 J/cm$^2$, about 15 J/cm$^2$ to 25 J/cm$^2$, or about 10 to about 20 J/cm$^2$.

In certain embodiments, the silicone-based biophotonic composition may be re-illuminated at certain intervals. In yet another embodiment, the source of actinic light is in continuous motion over the treated area for the appropriate time of exposure. In yet another embodiment, the silicone-based biophotonic composition may be illuminated until the silicone-based biophotonic composition is at least partially photobleached or fully photobleached.

In certain embodiments, the chromophore(s) may be photoexcited by ambient light including from the sun and overhead lighting. In certain embodiments, the chromophore(s) may be photoactivated by light in the visible range of the electromagnetic spectrum. The light may be emitted by any light source such as sunlight, light bulb, an LED device, electronic display screens such as on a television, computer, telephone, mobile device, flashlights on mobile devices. In the methods of the present disclosure, any source of light can be used. For example, a combination of ambient light and direct sunlight or direct artificial light may be used. Ambient light can include overhead lighting such as LED bulbs, fluorescent bulbs etc, and indirect sunlight.

In the methods of the present disclosure, the silicone-based biophotonic composition may be removed from the skin following application of light. In other embodiments, the silicone-based biophotonic composition is left on the tissue for an extended period of time and re-activated with direct or ambient light at appropriate times to treat the condition.

In certain embodiments of any of the foregoing or following, the silicone-based biophotonic composition, such as a silicone-based biophotonic membrane, has a removable cover for covering one or both sides of the membrane. The removable cover may be peelable. The removable cover may comprise a sheet or a film of material, such as paper or foil. In certain embodiments, the removable cover is opaque and can protect the membrane from illumination until the treatment time. The cover may be partially removable. In certain embodiments, the cover may be re-applicable to the membrane surface, such as after a treatment time, in order to protect the membrane from further illumination in between treatments.

In certain embodiments of the method of the present disclosure, the silicone-based biophotonic composition may be applied to the tissue, such as on the face, once, twice, three times, four times, five times or six times a week, daily, or at any other frequency. The total treatment time may be one week, two weeks, three weeks, four weeks, five weeks, six weeks, seven weeks, eight weeks, nine weeks, ten weeks, eleven weeks, twelve weeks, or any other length of time deemed appropriate. In certain embodiments, the total tissue area to be treated may be split into separate areas (cheeks, forehead), and each area treated separately. For example, the silicone-based biophotonic composition may be applied topically to a first portion, and that portion illuminated with light, and the composition then removed. Then the silicone-based biophotonic composition is applied to a second portion, illuminated and removed. Finally, the silicone-based biophotonic composition is applied to a third portion, illuminated and removed.

In certain embodiments, the silicone-based biophotonic composition can be used following wound closure to optimize scar revision. In this case, the silicone-based biophotonic composition may be applied at regular intervals such as once a week, or at an interval deemed appropriate by the physician.

In certain embodiments, the silicone-based biophotonic composition may be used following ablative skin rejuvenation treatment to maintain the condition of the treated skin. In this case, the silicone-based biophotonic composition may be applied at regular intervals such as once a week, or at an interval deemed appropriate by the physician.

In the methods of the present disclosure, additional components may optionally be included with the silicone-based biophotonic compositions or used in combination with the silicone-based biophotonic compositions. Such additional components may include, but are not limited to, healing factors, antimicrobials, oxygen-rich agents, wrinkle fillers such as botox, hyaluronic acid and polylactic acid, fungal, anti-bacterial, anti-viral agents and/or agents that promote collagen synthesis. These additional components may be applied to the skin in a topical fashion, prior to, at the same time of, and/or after topical application of the silicone-based biophotonic compositions of the present disclosure. Suitable healing factors comprise compounds that promote or enhance the healing or regenerative process of the tissues on the application site. During the photoactivation of a silicone-based biophotonic composition of the present disclosure, there may be an increase of the absorption of molecules of such additional components at the treatment site by the skin or the mucosa. Healing factors may also modulate the biophotonic effect resulting from the silicone-based biophotonic composition. Suitable healing factors include, but are not limited to glucosamines, allantoins, saffron, agents that promote collagen synthesis, anti-fungal, anti-bacterial, anti-viral agents and wound healing factors such as growth factors.

(i) Skin Rejuvenation

The silicone-based biophotonic compositions of the present disclosure may be useful in promoting skin rejuvenation or improving skin condition and appearance. The dermis is the second layer of skin, containing the structural elements of the skin, the connective tissue. There are various types of connective tissue with different functions. Elastin fibers give the skin its elasticity, and collagen gives the skin its strength.

The junction between the dermis and the epidermis is an important structure. The dermal-epidermal junction interlocks forming finger-like epidermal ridges. The cells of the epidermis receive their nutrients from the blood vessels in the dermis. The epidermal ridges increase the surface area of the epidermis that is exposed to these blood vessels and the needed nutrients.

The aging of skin comes with significant physiological changes to the skin. The generation of new skin cells slows down, and the epidermal ridges of the dermal-epidermal junction flatten out. While the number of elastin fibers increases, their structure and coherence decreases. Also the amount of collagen and the thickness of the dermis decrease with the ageing of the skin.

Collagen is a major component of the skin's extracellular matrix, providing a structural framework. During the aging process, the decrease of collagen synthesis and insolubilization of collagen fibers contribute to a thinning of the dermis and loss of the skin's biomechanical properties.

The physiological changes to the skin result in noticeable aging symptoms often referred to as chronological-, intrinsic- and photo-aging. The skin becomes drier, roughness and scaling increase, the appearance becomes duller, and most obviously fine lines and wrinkles appear. Other symptoms or signs of skin aging include, but are not limited to, thinning and transparent skin, loss of underlying fat (leading to hollowed cheeks and eye sockets as well as noticeable loss of firmness on the hands and neck), bone loss (such that bones shrink away from the skin due to bone loss, which causes sagging skin), dry skin (which might itch), inability to sweat sufficiently to cool the skin, unwanted facial hair, freckles, age spots, spider veins, rough and leathery skin, fine wrinkles that disappear when stretched, loose skin, a blotchy complexion.

The dermal-epidermal junction is a basement membrane that separates the keratinocytes in the epidermis from the extracellular matrix, which lies below in the dermis. This membrane consists of two layers: the basal lamina in contact with the keratinocytes, and the underlying reticular lamina in contact with the extracellular matrix. The basal lamina is rich in collagen type IV and laminin, molecules that play a role in providing a structural network and bioadhesive properties for cell attachment.

Laminin is a glycoprotein that only exists in basement membranes. It is composed of three polypeptide chains (alpha, beta and gamma) arranged in the shape of an asymmetric cross and held together by disulfide bonds. The three chains exist as different subtypes which result in twelve different isoforms for laminin, including Laminin-1 and Laminin-5.

The dermis is anchored to hemidesmosomes, specific junction points located on the keratinocytes, which consist of a-integrins and other proteins, at the basal membrane keratinocytes by type VII collagen fibrils. Laminins, and particularly Laminin-5, constitute the real anchor point between hemidesmosomal transmembrane proteins in basal keratinocytes and type VII collagen.

Laminin-5 synthesis and type VII collagen expression have been proven to decrease in aged skin. This causes a loss of contact between dermis and epidermis, and results in the skin losing elasticity and becoming saggy.

Recently another type of wrinkles, generally referred to as expression wrinkles, received general recognition. Expression wrinkles result from a loss of resilience, particularly in the dermis, because of which the skin is no longer able to resume its original state when facial muscles which produce facial expressions.

The silicone-based biophotonic compsoitions of the present disclosure and methods of the present disclosure promote skin rejuvenation. In certain embodiments, the silicone-based biophotonic compositions and methods of the present disclosure may promote skin conditioning such as skin luminosity, reduction of pore size, reducing blotchiness, making even skin tone, reducing dryness, and tightening of the skin. In certain embodiments, the silicone-based biophotonic compositions and methods of the present disclosure may promote collagen synthesis. In certain other embodiments, the silicone-based biophotonic compositions and methods of the present disclosure may reduce, diminish, retard or even reverse one or more signs of skin aging including, but not limited to, appearance of fine lines or wrinkles, thin and transparent skin, loss of underlying fat (leading to hollowed cheeks and eye sockets as well as noticeable loss of firmness on the hands and neck), skin aging due bone loss (wherein bones shrink away from the skin due to bone loss, which causes sagging skin), dry skin (which might itch), inability to sweat sufficiently to cool the skin, unwanted facial hair, freckles, age spots, spider veins, rough and leathery skin, fine wrinkles that disappear when stretched, loose skin, or a blotchy complexion. In certain embodiments, the silicone-based biophotonic compositions and methods of the present disclosure may induce a reduction in pore size, enhance sculpturing of skin subsections, and/or enhance skin translucence.

In certain embodiments, the silicone-based biophotonic composition may be used in conjunction with collagen promoting agents. Agents that promote collagen synthesis (i.e., pro-collagen synthesis agents) include amino acids, peptides, proteins, lipids, small chemical molecules, natural products and extracts from natural products.

For instance, it has been discovered that intake of vitamin C, iron, and collagen can effectively increase the amount of collagen in skin or bone. See, e.g., U.S. Patent Application Publication 20090069217. Examples of the vitamin C include an ascorbic acid derivative such as L-ascorbic acid or sodium L-ascorbate, an ascorbic acid preparation obtained by coating ascorbic acid with an emulsifier or the like, and a mixture containing two or more of those vitamin Cs at an arbitrary rate. In addition, natural products containing vitamin C such as acerola or lemon may also be used.

Examples of the iron preparation include: an inorganic iron such as ferrous sulfate, sodium ferrous citrate, or ferric pyrophosphate; an organic iron such as heme iron, ferritin iron, or lactoferrin iron; and a mixture containing two or more of those irons at an arbitrary rate. In addition, natural products containing iron such as spinach or liver may also be used. Moreover, examples of the collagen include: an extract obtained by treating bone, skin, or the like of a mammal such as bovine or swine with an acid or alkaline; a peptide obtained by hydrolyzing the extract with a protease such as pepsin, trypsin, or chymotrypsin; and a mixture containing two or more of those collagens at an arbitrary rate. Collagens extracted from plant sources may also be used.

(ii) Skin Disorders

The silicone-based biophotonic compositions and methods of the present disclosure may be used in a treatment of a skin disorder that may include, but is not limited to, erythema, telangiectasia, actinic telangiectasia, basal cell carcinoma, contact dermatitis, dermatofibrosarcoma protuberans, genital warts, hidradenitis suppurativa, melanoma, merkel cell carcinoma, nummular dermatitis, molloscum contagiosum, psoriasis, psoriatic arthritis, rosacea, scabies, scalp psoriasis, sebaceous carcinoma, squamous cell carcinoma, seborrheic dermatitis, seborrheic keratosis, shingles, tinea *versicolor*, warts, skin cancer, pemphigus, sunburn, dermatitis, eczema, rashes, impetigo, lichen simplex chronicus, rhinophyma, perioral dermatitis, pseudofolliculitis barbae, erythema multiforme, erythema nodosum, granuloma annulare, actinic keratosis, purpura, alopecia areata, aphthous stomatitis, drug eruptions, dry skin, chapping, xerosis, ichthyosis vulgaris, fungal infections, herpes simplex, intertrigo, keloids, keratoses, milia, moluscum contagiosum, *pityriasis rosea*, pruritus, urticaria, and vascular tumors and malformations. Dermatitis includes contact dermatitis, atopic dermatitis, seborrheic dermatitis, nummular dermatitis, generalized exfoliative dermatitis, and statis dermatitis. Skin cancers include melanoma, basal cell carcinoma, and squamous cell carcinoma.

(iii) Acne and Acne Scars

The silicone-based biophotonic compositions and methods of the present disclosure may be used to treat acne. As used herein, "acne" means a disorder of the skin caused by inflammation of skin glands or hair follicles. The silicone-based biophotonic compositions and methods of the disclosure can be used to treat acne at early pre-emergent stages or later stages where lesions from acne are visible. Mild, moderate and severe acne can be treated with embodiments of the silicone-based biophotonic compositions and methods. Early pre-emergent stages of acne usually begin with an excessive secretion of sebum or dermal oil from the sebaceous glands located in the pilosebaceous apparatus. Sebum reaches the skin surface through the duct of the hair follicle. The presence of excessive amounts of sebum in the duct and on the skin tends to obstruct or stagnate the normal flow of sebum from the follicular duct, thus producing a thickening and solidification of the sebum to create a solid plug known as a comedone. In the normal sequence of developing acne, hyperkeratinazation of the follicular opening is stimulated, thus completing blocking of the duct. The usual results are papules, pustules, or cysts, often contaminated with bacteria, which cause secondary infections. Acne is characterized particularly by the presence of comedones, inflammatory papules, or cysts. The appearance of acne may range from slight skin irritation to pitting and even the development of disfiguring scars. Accordingly, the silicone-based biophotonic compositions and methods of the present disclosure can be used to treat one or more of skin irritation, pitting, development of scars, comedones, inflammatory papules, cysts, hyperkeratinazation, and thickening and hardening of sebum associated with acne.

Some skin disorders present various symptoms including redness, flushing, burning, scaling, pimples, papules, pustules, comedones, macules, nodules, vesicles, blisters, telangiectasia, spider veins, sores, surface irritations or pain, itching, inflammation, red, purple, or blue patches or discolorations, moles, and/or tumors.

The silicone-based biophotonic compositions and methods of the present disclosure may be used to treat various types of acne. Some types of acne include, for example, acne vulgaris, cystic acne, acne atrophica, bromide acne, chlorine acne, acne conglobata, acne cosmetica, acne detergicans, epidemic acne, acne estivalis, acne fulminans, halogen acne, acne indurata, iodide acne, acne keloid, acne mechanica, acne papulosa, pomade acne, premenstral acne, acne *pustulosa*, acne scorbutica, acne scrofulosorum, acne urticata, acne varioliformis, acne *venenata*, propionic acne, acne excoriee, gram negative acne, steroid acne, and nodulocystic acne.

In certain embodiments, the silicone-based biophotonic compositions of the present disclosure is used in conjunction with systemic or topical antibiotic treatment. For example, antibiotics used to treat acne include tetracycline, erythromycin, minocycline, doxycycline, which may also be used with the compositions and methods of the present disclosure. The use of the silicone-based biophotonic composition can reduce the time needed for the antibiotic treatment or reduce the dosage.

(iv) Wound Healing

The silicone-based biophotonic compositions and methods of the present disclosure may be used to treat wounds, promote wound healing, and promote tissue. Wounds that may be treated by the silicone-based biophotonic compositions and methods of the present disclosure include, for example, injuries to the skin and subcutaneous tissue initiated in different ways (e.g., pressure ulcers from extended bed rest, wounds induced by trauma or surgery, burns, ulcers linked to diabetes or venous insufficiency, wounds induced by conditions such as periodontitis) and with varying characteristics. In certain embodiments, the present disclosure provides silicone-based biophotonic compositions and methods for treating and/or promoting the healing of, for example, burns, incisions, excisions, lesions, lacerations, abrasions, puncture or penetrating wounds, surgical wounds, contusions, hematomas, crushing injuries, amputations, sores and ulcers.

Silicone-based biophotonic compositions and methods of the present disclosure may be used to treat and/or promote the healing of chronic cutaneous ulcers or wounds, which are wounds that have failed to proceed through an orderly and timely series of events to produce a durable structural, functional, and cosmetic closure. The vast majority of chronic wounds can be classified into three categories based on their etiology: pressure ulcers, neuropathic (diabetic foot) ulcers and vascular (venous or arterial) ulcers.

For example, the present disclosure provides silicone-based biophotonic compositions and methods for treating and/or promoting healing of a diabetic ulcer. Diabetic patients are prone to foot and other ulcerations due to both neurologic and vascular complications. Peripheral neuropathy can cause altered or complete loss of sensation in the foot and/or leg. Diabetic patients with advanced neuropathy lose all ability for sharp-dull discrimination. Any cuts or trauma to the foot may go completely unnoticed for days or weeks in a patient with neuropathy. A patient with advanced neuropathy loses the ability to sense a sustained pressure insult, as a result, tissue ischemia and necrosis may occur leading to for example, plantar ulcerations. Microvascular disease is one of the significant complications for diabetics which may also lead to ulcerations. In certain embodiments, silicone-based biophotonic compositions and methods of treating a chronic wound are provided here in, where the chronic wound is characterized by diabetic foot ulcers and/or ulcerations due to neurologic and/or vascular complications of diabetes.

In other examples, the present disclosure provides silicone-based biophotonic compositions and methods for treating and/or promoting healing of a pressure ulcer. Pressure ulcers include bed sores, decubitus ulcers and ischial tuberosity ulcers and can cause considerable pain and discomfort to a patient. A pressure ulcer can occur as a result of a prolonged pressure applied to the skin. Thus, pressure can be exerted on the skin of a patient due to the weight or mass of an individual. A pressure ulcer can develop when blood supply to an area of the skin is obstructed or cut off for more than two or three hours. The affected skin area can turn red, become painful and necrotic. If untreated, the skin can break open and become infected. A pressure ulcer is therefore a skin ulcer that occurs in an area of the skin that is under pressure from e.g. lying in bed, sitting in a wheelchair, and/or wearing a cast for a prolonged period of time. Pressure ulcers can occur when a person is bedridden, unconscious, unable to sense pain, or immobile. Pressure ulcers often occur in boney prominences of the body such as the buttocks area (on the sacrum or iliac crest), or on the heels of foot.

There are three distinct phases in the wound healing process. First, in the inflammatory phase, which typically occurs from the moment a wound occurs until the first two to five days, platelets aggregate to deposit granules, promoting the deposit of fibrin and stimulating the release of growth factors. Leukocytes migrate to the wound site and begin to digest and transport debris away from the wound. During this inflammatory phase, monocytes are also converted to macrophages, which release growth factors for stimulating angiogenesis and the production of fibroblasts.

Second, in the proliferative phase, which typically occurs from two days to three weeks, granulation tissue forms, and epithelialization and contraction begin. Fibroblasts, which are key cell types in this phase, proliferate and synthesize collagen to fill the wound and provide a strong matrix on which epithelial cells grow. As fibroblasts produce collagen, vascularization extends from nearby vessels, resulting in granulation tissue. Granulation tissue typically grows from the base of the wound. Epithelialization involves the migration of epithelial cells from the wound surfaces to seal the wound. Epithelial cells are driven by the need to contact cells of like type and are guided by a network of fibrin strands that function as a grid over which these cells migrate. Contractile cells called myofibroblasts appear in wounds, and aid in wound closure. These cells exhibit collagen synthesis and contractility, and are common in granulating wounds.

Third, in the remodeling phase, the final phase of wound healing which can take place from three weeks up to several years, collagen in the scar undergoes repeated degradation and re-synthesis. During this phase, the tensile strength of the newly formed skin increases.

However, as the rate of wound healing increases, there is often an associated increase in scar formation. Scarring is a consequence of the healing process in most adult animal and human tissues. Scar tissue is not identical to the tissue which it replaces, as it is usually of inferior functional quality. The types of scars include, but are not limited to, atrophic, hypertrophic and keloidal scars, as well as scar contractures. Atrophic scars are flat and depressed below the surrounding skin as a valley or hole. Hypertrophic scars are elevated scars that remain within the boundaries of the original lesion, and often contain excessive collagen arranged in an abnormal pattern. Keloidal scars are elevated scars that spread beyond the margins of the original wound and invade the surrounding normal skin in a way that is site specific, and often contain whorls of collagen arranged in an abnormal fashion.

In contrast, normal skin consists of collagen fibers arranged in a basket-weave pattern, which contributes to both the strength and elasticity of the dermis. Thus, to achieve a smoother wound healing process, an approach is needed that not only stimulates collagen production, but also does so in a way that reduces scar formation.

Certain embodiments of the silicone-based biophotonic compositions and methods of the present disclosure may promote wound healing by promoting the formation of substantially uniform epithelialization; promoting collagen synthesis; promoting controlled contraction; and/or by reducing the formation of scar tissue. In certain embodiments, the biophotonic compositions and methods of the present disclosure may promote wound healing by promoting the formation of substantially uniform epithelialization. In some embodiments, the silicone-based biophotonic compositions and methods of the present disclosure may modulate or promote collagen synthesis. In some other embodiments, the silicone-based biophotonic compositions and methods of the present disclosure may promote controlled contraction. In certain embodiments, the silicone-based biophotonic compositions and methods of the present disclosure may promote wound healing, for example, by reducing the formation of scar tissue.

In the methods of the present disclosure, the silicone-based biophotonic compositions of the present disclosure may also be used in combination with negative pressure assisted wound closure devices and systems.

In certain embodiments, the silicone-based biophotonic composition is kept in place for up to one, two or 3 weeks, and illuminated with light which may include ambient light at various intervals. In this case, the silicone-based biophotonic composition may be covered up in between exposure to light with an opaque material or left exposed to light.

(6) Kits

The present disclosure also provides kits for preparing a silicone-based biophotonic compositions and/or providing any of the components required for forming silicone-based biophotonic compositions of the present disclosure.

In some embodiments, the kit includes containers comprising the components or compositions that can be used to make the silicone-based biophotonic compostions of the present disclosure. In some embodiments, the kit includes the silicone-based biophotonic composition of the present disclosure. The different components making up the silicone-based biophotonic compositions of the present disclosure may be provided in separate containers. For example, the surfactant phase may be provided in a container separate from the silicone phase. Examples of such containers are dual chamber syringes, dual chamber containers with removable partitions, sachets with pouches, and multiple-compartment blister packs. Another example is one of the components being provided in a syringe which can be injected into a container of another component.

In other embodiments, the kit comprises a systemic drug for augmenting the treatment of the silicone-based biophotonic composition of the present disclosure. For example, the kit may include a systemic or topical antibiotic, hormone treatment (e.g. for acne treatment or wound healing), or a negative pressure device.

In other embodiments, the kit comprises a means for mixing or applying the components of the silicone-based biophotonic compositions.

In certain embodiments of the kit, the kit may further comprise a light source such as a portable light with a wavelength appropriate to activate the chromophore of the silicone-based biophotonic composition. The portable light may be battery operated or re-chargeable.

Written instructions on how to use the silicone-based biophotonic compositions in accordance with the present disclosure may be included in the kit, or may be included on or associated with the containers comprising the silicone-based biophotonic composition or the components making up the silicone-based biophotonic compositions of the present disclosure.

Identification of equivalent silicone-based biophotonic compositions, methods and kits are well within the skill of the ordinary practitioner and would require no more than routine experimentation, in light of the teachings of the present disclosure.

Variations and modifications will occur to those of skill in the art after reviewing this disclosure. The disclosed features may be implemented, in any combination and sub-combinations (including multiple dependent combinations and sub-combinations), with one or more other features described herein. The various features described or illustrated above, including any components thereof, may be combined or integrated in other systems. Moreover, certain features may be omitted or not implemented. Examples of changes, substitutions, and alterations are ascertainable by one skilled in the art and could be made without departing from the scope of the information disclosed herein. All references cited herein are incorporated by reference in their entirety and made part of this application.

Practice of the disclosure will be still more fully understood from the following examples, which are presented herein for illustration only and should not be construed as limiting the disclosure in any way.

EXAMPLES

Example 1: Silicone-Based Biophotonic Composition (25% Pluronic-F127)

Preparation of 25% Wt % Pluronic-F127 Solutions (Surfactant Phase)

Typical preparation of thermogelling solutions of Pluronic comprised dissolving a measured mass of Pluronic F-127 in a measured volume of cold, de-ionised water (~4° C.). The concentration of Pluronic is expressed in weight per volume of $H_2O$.

Thus, for the preparation of a stock thermogelling Pluronic solution (25% w/v), a mass of 25.00 g of Pluronic F-127 was added, under magnetic stirring, to 100 mL of $H_2O$ in an Erlenmeyer flask of 250 mL. The Erlenmeyer with the solution was then cooled in an ice bath (between 2 and 4° C.), while continuing stirring for about 1 hour, until complete dissolution of the Pluronic F-127. The resulting solution was then stored in the fridge at about 4° C.

A gelation test was performed which indicated that the solution formed into a hydrogel after approximately 5 minutes at room temperature (~22° C.).

Preparation of Silicone-15/85 (Silicone Phase)

A silicone-15/85 component for the silicone-based biophotonic was prepared by mixing 15% of Sylgard-184 elastomer kit and 85% of Sylgard-527 gel kit. Thus, typical mixture of silicone-15/85 was prepared by thoroughly mixing 2.667 g of Sylgard-184 (composed of 2.423 g of part A of the Sylgard-184 kit and 0.244 g of part B of the Sylgard-184 kit), with 15.151 g of Sylgard-527 (composed of 7.574 g of part A of the Sylgard-527 kit and 7.577 g of part B of the Sylgard-527 kit). The silicone-15/85 mixture was cooled down to −4° C. in order to maintain it in a liquid form.

Preparation of the Silicone-Based Biophotonic Composition

To form the silicone-based biophotonic composition, 2.0 mL of the cold Pluronic-F127 themogelling solution containing 0.327 mg of Eosin Y and 0.327 g of Fluorescein was added to 9.221 g of the silicone-15/85 mixture, freshly prepared, under vigorous stirring in order to create an extremely fine emulsion. Thereafter, in order to form a silicone-based biophotonic membrane, the resulting mixture was cast onto petri dishes. The cast amount was controlled so as to obtain a membrane thickness of 2 mm. The casted, silicone-based biophotonic membrane mixture was then cured for 5 hours at 40° C. and under humid atmosphere in an incubator.

The emulsion that was formed on completion of the mixing of the surfactant phase and the silicone phase was a very fine and highly-stable micro-emulsion or gel. Without being bound to a particular theory, it was thought that these properties of the micro-emulsion may have resulted from the hydrophobic nature of silicone and the surfactant properties of Pluronic-F127 When cast in the Pertri dish and after curing, the resulting silicone-based biophotonic membrane was homogeneous and flexible. The membrane was thereafter tested to evaluate whether the chromophores (Eosin Y and fluorescein) might leach from the silicone-based biophotonic membrane, as sample of the membrane was immersed in a phosphate-buffered saline (PBS) solution for 24 hours and no leaching of the chromophores was observed In a second experiment, 0.75 mL of Pluronic-F127 thermogelling solution containing 0.123 mg of Eosin Y and 0.123 mg of fluorescein was added to 6.744 g of silicone-15/85 (prepared as described above) under vigorous stirring. The resultant uniform microemulsion was extremely fine and showed high stability. Aliquots of the micro-emulsion were casted onto petri dishes so as to obtain a thickness of 2 mm, then cured for 5 hours at 40° C. and under humid atmosphere in an incubator.

Light emitted through and by a silicone-based biophotonic membrane prepared from this second experiment was measured using a SP-100 spectroradiometer (SP-100, ORB Optronix) whilst being illuminated with light having a peak emission wavelength of 450 nm (peak wavelength ranging between 400-470 nm and a power density of about 30-150 mW/cm$^2$) for 5 minutes. As can be seen in FIGS. 1-4, the chromophores did not fully photobleach after 15 minutes of illumination in 5 minute intervals.

Example 2—Cytokines and Growth Factors in DHF

In order to gain a more detailed picture of the biological effect mediated by the silicone-based biophotonic membrane of Example 1 (second experiment), Human Cytokine Antibody Array (RayBio C-Series, RayBiotech, Inc.) was performed. Cytokines broadly defined as secreted cell-cell signaling proteins play important roles in inflammation, innate immunity, apoptosis, angiogenesis, cell growth and differentiation. Simultaneous detection of multiple cytokines provides a powerful tool to study cell activity. Regulation of cellular processes by cytokines is a complex, dynamic process, often involving multiple proteins. Positive and negative feedback loops, pleiotrophic effects and redundant functions, spatial and temporal expression of or synergistic interactions between multiple cytokines, even regulation via release of soluble forms of membrane-bound receptors, are all common mechanisms modulating the effects of cytokine signaling.

DHF (Derman Human Fibroblast) and THP1(human acute monocytic leukemia cells) were used as an in vitro model to study the effect of the blue light in combination with the light emitted by the silicone-based biophotonic membrane on the secretion of the inflammatory cytokines, chemokines and growth factors. Excessive, uncontrolled inflammation is detrimental to the host and can impair wound healing processes amongst other things. The purpose of this study was to demonstrate that blue light in combination with the fluorescence emitted by the silicone-based biophotonic membrane(s) is able to down-regulate the production of pro-inflammatory cytokines and chemokines and improve/accelerate the healing process.

Briefly, a non-toxic concentration of TGF β-1 was used to stimulate DHF cells, and IFNγ and LPS were used to stimulate PMA-treated THP-1 cells. The membrane of Example 1 (second experiment) was then positioned 5 cm above the cell cultures and illuminated with blue light (450 nm).

Cell culture mediums were collected 24 h post-illumination and incubated with arrayed antibody membranes according to manufacturer instructions (Human Cytokine Antibody Array, RayBio C-series from Raybiotech). Signals were quantified with Image J® software. For each experiment, the XTT assay (cell viability assay) was performed to normalize the quantity of cytokine secreted to the cell viability (in all cases the viability was over 90% showing a non-toxic effect of the treatment). All samples were done in quadruplets.

The effect of illuminated membrane on cytokines and growth factor secretion in DHF and THP-1 cells is summarized in the Tables 1 and 2 below.

TABLE 1

Modulation of protein expression in Dermal Human Fibroblasts activated by TGFB1 24 hours after treatment with blue light + silicone-based biophotonic membrane compared to control untreated cells.

| Cytokines | Silicone-based bipohotonic membrane |
|---|---|
| IL2 | — |
| IL3 | ↓↓↓ |
| IL4 | ↑ |
| IL6 | — |
| IL8 | ↓↓↓ |
| IL10 | ↑↑↑ |
| IL12 p40/70 | — |
| IL13 | ↓ |
| IL15 | ↑ |
| TNF-alpha | ↓ |
| TNF-beta | ↓↓↓ |
| IL1-alpha | ↓↓↓ |
| IL1-beta | ↓↓ |
| IFN-gamma | ↓↓↓ |
| MCP1 | ↓↓↓ |
| MCP2 | ↓↓↓ |
| MCP3 | ↑ |
| M-CSF | ↓↓↓ |
| MDC | — |
| MIG | ↑↑↑ |
| MIP-1-delta | ↓↓↓ |
| RANTES | ↓↓↓ |
| TARC | ↑ |
| Growth Factors | |
| EGF | — |
| IGF-1 | ↑↑↑ |
| ANG | ↑↑↑ |
| VEGF | ↑↑↑ |
| PDGF-BB | ↓↓↓ |
| ENA-78 | ↓↓↓ |
| G-CSF | ↑↑↑ |
| GM-CSF | ↓↓↓ |
| GRO | ↓↓↓ |
| GRO-alpha | ↓↓↓ |
| TGFbeta1 | ↓↓↓ |
| Leptin | — |

↓ less than 25% decrease
↓↓ 25-50% decrease
↓↓↓ more than 50% decrease
— No modulation
↑ less than 25% increase
↑↑ 25-50% increase
↑↑↑ more than 50% increase

TABLE 2

Modulation of protein expression in THP1 cells differentiated into macrophages 24 hours after treatment with blue light + silicone-based biophotonic membrane compared to control untreated cells.

| | Silicone-based biophotonic membrane |
|---|---|
| Cytokines | |
| IL2 | — |
| IL3 | ↓↓↓ |
| IL4 | — |
| IL6 | ↓↓↓ |
| IL8 | ↓↓ |
| IL10 | ↑↑↑ |
| IL12 p40/70 | — |
| IL13 | — |
| IL15 | ↑ |
| TNF-alpha | ↓↓↓ |
| TNF-beta | — |
| IL1-alpha | ↓ |
| IL1-beta | ↓↓↓ |
| IFN-gamma | — |
| MCP1 | ↑↑ |
| MCP2 | ↓↓↓ |
| MCP3 | — |
| M-CSF | — |
| MDC | — |
| MIG | — |
| MIP-1-delta | — |
| RANTES | ↓↓ |
| TARC | ↑ |
| Growth Factors | |
| EGF | — |
| IGF-1 | — |
| ANG | — |
| VEGF | ↑ |
| PDGF-BB | ↑ |
| ENA-78 | — |
| G-CSF | — |
| GM-CSF | ↓↓↓ |
| GRO | ↓↓ |
| GRO-alpha | ↓ |
| TGFbeta1 | — |
| Leptin | ↑ |

↓ less than 25% decrease
↓↓ 25-50% decrease
↓↓↓ more than 50% decrease
— No modulation
↑ less than 25% increase
↑↑ 25-50% increase
↑↑↑ more than 50% increase Results from the cytokine/chemokine array assay revealed that the treatment with the silicone-based biophotonic membrane of Example 1 negatively modulated pro-inflammatory cytokines (such as TNF alpha, IL-6, IL-8, IL-1 alpha, IL-1 beta, IFNγ) and pro-inflammatory chemokines (such as MCP-1, -2, RANTES, GRO,) production. The results also indicated that the treatment utilizing the silicone-based biophotonic membrane demonstrated an ability to negatively modulate growth factors secretion (such as TGF-beta1, and PDGF-BB) in DHF cells.

Example 3—Proliferation Level in DHF Cells Upon Illumination by a Silicone-Based Biophotonic Membrane In order to gain more detailed picture of the biological effect mediated by the silicone-based biophotonic membrane of Example 1 (second experiment) and its implication in a wound healing process, cellular proliferation was assessed in Human Dermal Fibroblast (DHF) experimental system. In tissues, within four-five days upon injury, matrix-generating cells i.e. fibroblasts, move into the granulation tissue. Their migration to and proliferation within the wound site are prerequisites for wound granulation and consecutive healing. Fibroblasts then participate in the construction of scar tissue and its remodeling. Thus viable, actively dividing fibroblast are crucial player in healing progression.

The present experiment utilized an XTT assay to measure cell viability. The XTT-based method measures the mitochondrial dehydrogenase activity of proliferating cells. In brief, the mitochondrial dehydrogenases of viable cells reduce the tetrazolium ring of XTT, yielding an orange derivative, which is water soluble. The absorbance of the resulting orange solution is measured spectrophotometrically. An increase or decrease in cells number relative to control cells, results in an accompanying change in the amount of orange derivative, indicating the changes in the number of viable, dividing cells.

DHF cells were illuminated for 5 min with the silicone-based biophotonic membrane of Example 1. 24 h post-treatment XTT solution was added to the cells. Four hours later the absorbance of orange supernatant was measured spectrophotometrically. The difference in the number of actively proliferating fibroblasts as compared to non-illuminated control was calculated.

The XTT assay showed that the silicone membrane of Example 1 did not modulate DHF proliferation under the test conditions as compared to a control (non-treated cells).

Example 4—Evaluation of a Silicone-Based Biophotonic Thermogel of the Present Description for a Prevention of Scarring Hypertrohic scars (HTS) result from excessive dermal fibrosis involving myofibroblasts. They occur after an injury to the dermis. In addition to their disfiguring characteristic, scars can be itchy, rigid and painful. Excessive production of collagen and other extracellular matrix (ECM) proteins and/or deficient degradation and remodeling of ECM are the main causes of scar formation. These phenomenon occur when the inflammatory response to injury is prolonged. In HTS, the growth factors, TGFβ1 and PDGF are over expressed by fibroblasts. They are major proteins in HTS (Avouac J, et al. *Inhibition of activator protein 1 signaling abrogates transforming growth factor b-mediated activation of fibroblasts and prevents experimental fibrosis*. Arthritis Rheumatism, 2012, volume 64:1642-4652; Trojanowska M, Role of PDGF in fibrotic diseases and systemic sclerosis. Rheumatology, 2008, volume 47: v2-v4). TGFb1 is responsible for the excessive collagen secretion and the reduction of matrix metalloproteinases (MMPs) such as collagenase (Cutroneo K R. *TGF-beta-induced fibrosis and SMAD signaling: oligo decoys as natural therapeutics for inhibition of tissue fibrosis and scarring.*, Wound Rep Regen 2007, volume 15: S54-60; Chen Z C, Raghunath M. *Focus on collagen: In vitro systems to study fibrogenesis and antifibrosis—state of the art*. Fibrogenesis Tissue Repair, 2009, volume 2: 7). PDGF is a potent chemoattractant for fibroblasts and constitutes a good target for the treatment of fibrosis (Beyer C, Distler J H W. *Tyrosine kinase signaling in fibrotic disorders. Translation of basic research to human disease*. Biochem Biophys Acta, 2013, volume 1832: 897-904). HTS have high expression of MMP-2 and low expression of MMP-9 (Gauglitz G G et al. *Hypertrophic scarring and keloids: pathomechanisms and current and emerging treatment strategies*. Mol Med, 2011; volume 17: 113-125).

Experimental Design a) Protein Secretion-Inflammatory Mediators, Cytokines, Growth Factors A Dermal Human Fibroblasts (DHF) cell culture model was used as in vitro model to study the effect of a treatment comprising of an illumination with an actinic light source emitting a non-coherent blue light upon a silicone-based biophotonic membrane containing the chromophores Eosin Y and fluorescein may have on the secretion of various proteins that function as inflammatory mediators, or growth factors, or which are involved in tissue remodeling (such as matrix metalloproteinases (MMPs), and tissue inhibitors of matrix metalloproteinases (TIMPs).

For this experimental model, the cells were illuminated for a period of 5 minutes using the above-described silicone-based biophotonic membrane together with a visible blue light (KLOX Multi-LED light) at the distance of 5 cm. The blue light and fluorescence dose received by the cells during the illumination time are presented in Table 3.

TABLE 3

Dose (J/cm2) of blue light and fluorescence received by the cells during 5 minutes illumination

| | |
|---|---|
| Purple | 10.95 |
| Blue | 6.33 |
| Green | 0.53 |
| Yellow | 0.25 |
| Orange | 0.15 |
| Red | 0.16 |
| Total J/cm2 | 18.37 |

DHF cells were cultured on a glass bottom dish (approximately 2 mm thickness). One hour prior to illumination, the cells were treated with non-toxic concentration of TGFβ1 (5 ng/ml) to induce the hyperproliferative state that is that is typically observed in the process of the formation of hypertrophic scars. TGFβ1 was maintained in the culture medium after the illumination to mimic the scarring condition through whole time during which the assay was performed. The silicone-based biophotonic membrane as described above was applied on the other side of the glass dish (i.e. on the exterior surface of the dish) and illuminated at 5 cm distance using blue visible light (KLOX Thera™ lamp). Cells were also treated with light alone, which served as an internal control to ensure that the combination of light with the silicone-based biophotonic membrane containing the Eosin Y and fluorescein chromophores exerted a biological effect compared to light alone. At 24-hours post-treatment, the supernatant was collected and arrays were performed to evaluate the inflammatory cytokines, chemokines and growth factors production profile resulting from the treatment. The lists of proteins analyzed for each antibody array are presented below in Tables 4 and 5.

Antibodies Array profiles

TABLE 4

Human Cytokine Antibody Array C3

| | A | B | C | D | E | F | G | H | I | J | K | L |
|---|---|---|---|---|---|---|---|---|---|---|---|---|
| 1 | POS | POS | NEG | NEG | ENA-78 | G-CSF | GM-CSF | GRO | GRO alpha | I-309 | IL-1 alpha | IL-1 beta |
| 2 | POS | POS | NEG | NEG | ENA-78 | G-CSF | GM-CSF | GRO | GRO alpha | I-309 | IL-1 alpha | IL-1 beta |
| 3 | IL-2 | IL-3 | IL-4 | IL-5 | IL-6 | IL-7 | IL-8 | IL-10 | IL-12 p40/70 | IL-13 | IL-15 | IFN gamma |
| 4 | IL-2 | IL-3 | IL-4 | IL-5 | IL-6 | IL-7 | IL-8 | IL-10 | IL-12 p40/70 | IL-13 | IL-15 | IFN gamma |
| 5 | MCP-1 | MCP-2 | MCP-3 | M-CSF | MDC | MIG | MIP-1 delta | RANTES | SCF | SDF-1 | TARC | TGF beta 1 |
| 6 | MCP-1 | MCP-2 | MCP-3 | M-CSF | MDC | MIG | MIP-1 delta | RANTES | SCF | SDF-1 | TARC | TGF beta 1 |
| 7 | TNF alpha | TNF beta | EGF | IGF-1 | ANG | OSM | THPO | VEGF | PDGF BB | Leptin | NEG | POS |
| 8 | TNF alpha | TNF beta | EGF | IGF-1 | ANG | OSM | THPO | VEGF | PDGF BB | Leptin | NEG | POS |

POS = Positive Control Spot
NEG = Negative Control Spot
BLANK = Blank Spot

TABLE 5

Human Growth Factor Antibody Array C1

| | A | B | C | D | E | F | G | H | I | J | K | L |
|---|---|---|---|---|---|---|---|---|---|---|---|---|
| 1 | POS | POS | NEG | NEG | AREG | bFGF | b-NGF | EGF | EGFR | FGF-4 | FGF-6 | FGF-7 |
| 2 | POS | POS | NEG | NEG | AREG | bFGF | b-NGF | EGF | EGFR | FGF-4 | FGF-6 | FGF-7 |
| 3 | G-CSF | GDNF | GM-CSF | HB-EGF | HGF | IGFBP1 | IGFBP2 | IGFBP3 | IGFBP4 | IGFBP6 | IGF-1 | IGF-1 sR |

TABLE 5-continued

Human Growth Factor Antibody Array C1

| | A | B | C | D | E | F | G | H | I | J | K | L |
|---|---|---|---|---|---|---|---|---|---|---|---|---|
| 4 | G-CSF | GDNF | GM CSF | HB EGF | HGF | IGFBP1 | IGFBP2 | IGFBP3 | IGFBP4 | IGFBP6 | IGF-1 | IGF-1 sR |
| 5 | IGF-2 | M-CSF | M-CSF R | NT-3 | NT-4 | PDGF R alpha | PDGF R beta | PDGF AA | PDGF AB | PDGF BB | PLGF | SCF |
| 6 | IGF-2 | M-CSF | M-CSF R | NT-3 | NT-4 | PDGF R alpha | PDGF R beta | PDGF AA | PDGF AB | PDGF BB | PLGF | SCF |
| 7 | SCF R | TGF alpha | TGF beta | TGF beta 2 | TGF beta 3 | VEGF | VEGF R2 | VEGF R3 | VEGF D | BLANK | BLANK | POS |
| 8 | SCF R | TGF alpha | TGF beta | TGF beta 2 | TGF beta 3 | VEGF | VEGF R2 | VEGF R3 | VEGF D | BLANK | BLANK | POS |

POS = Positive Control Spot
NEG = Negative Control Spot
BLANK = Blank Spot

To assess the potential cytotoxicity of the treatment, supernatants from the treated cell cultures were also screened for lactate dehydrogenase (LDH) activity. LDH is an intracellular enzyme that is released in the culture medium when the cell is damaged. It is a marker of cytotoxicity. The assay quantifies the LDH activity that reduces NAD to NADH. NADH is specifically detected by colorimetry.

b) Cell Proliferation (DHF Cell Cultures)

Prior to the treatment, cells were subjected to starvation conditions (medium deprived of serum and hormones) in order to be synchronised in G1 phase. Following synchronisation, the DHF were subjected to the treatment comprising the silicone-based biophotonic thermogel and blue light illumination (with the intensity of 14.4 J/cm$^2$ at 5 cm distance). Cells were monitored for their proliferation at 24 h, 48 h, and 72 h post-treatment using CyQUANT direct cell proliferation assay.

c) In vivo Study Using a Dermal Fibrotic Mouse—Human Skin Graft Model System

To evaluate the potential of the silicone-based biophotonic composition treatment of the present disclosure to promote wound healing and prevent scarring, an in vivo mouse model system was utilized, more particularly, a dermal fibrotic mouse model, in which the split thickness human skin transplanted to full thickness excision wounds on the back of nude mouse developed a thickened, raised, contracted scar resembling human HTS (see Montazi M et al. *A nude mouse model of hypertrophic scar shows morphologic and histologic characteristics of human hypertrophic scar*. Wound Rep Reg, 2013, volume 21: 77-87).

To evaluate the treatment comprising the silicone-based biophotonic composition (containing Eosin Y and fluorescein) (prepared as per Example 1, experiment number 2 described above) and the visible blue light (KLOX Multi LED light) illumination, the biophotonic composition-light illumination treatment was applied (either in the form of an unpolymerized gel or as a polymerized membrane) using the illumination times and distance as described for the in vitro experiments of this Example 4, however in this in vivo system the biophonic composition was applied to be in topical (physical) contact to the skin grafted wounds. Treatment with the light-biophotonic composition began at day 7 post-transplantation with the mice being under a light general anesthesia via halothane nasal application. The treatment was done twice per week for a period of 3 weeks. The animals were sacrificed one week after the last treatment. Control animals did not receive the treatment and another group received the blue light only. The wounds were monitored by digital photography weekly before the animals were euthanized at the 4 weeks post-treatment point and the excised xenografts were examined.

The quantification of scar thickness and vascularity were done on hematoxylin & eosin (H&E) stained section images. Using Image J, the measurements of dermal thickness were done in high power images, with the dermal thickness being the distance between the epidermal-dermal junction and the dermal-adipose layer junction. Three measurements were taken per sample. The degree of vascularity was assessed by counting the number of blood vessels in five high power fields (HPFs) of the dermis.

Masson's Trichrome staining (as known in the art) was used to detect collagen fibers in the dermis. Using polarized light microscopy to examine the stained specimens, collagen fibers could be observed as being green in color, while nuclei appeared in black and cytoplasm and keratin in red.

Results a) Effect of a Silicone-Based Biophotonic Membrane with Blue Light Illumination Treatment on Production of Inflammatory Mediators Production in DHF Cells At 24 h post-treatment supernatant was collected and inflammatory cytokine array was performed to evaluate the inflammatory cytokines production profile upon silicone-based biophotonic membrane (containing Eosin Y and fluorescein) treatment in combination with KLOX Multi-LED light. The results of the array are summarized in Table 6.

Analysis of LDH activity showed that no significant cytotoxic effect of the treatment was observed in all of the silicone-based biophotonic membrane illuminated samples.

TABLE 6

Summary of significant up (↑) and down-regulation (↓) observed in inflammatory mediators production (cytokines in red, chemokines in blue) and growth factors (in black) compared to non-treated controls.

| Decrease | Increase |
|---|---|
| IL-3, IL-8, TNFβ, IL-1α, IL-1β, IFNγ, MCP1 MCP2, M-CSF, MIP1δ, RANTES, GRO, GROα PDGF-BB, ENA-78, GM-CSF, TGFβ1 | IL-10, MIG, IGF1, ANG, VEGF, G-CSF |

PDGF-BB and TGFb1 and important growth factors implicated in the pathogenesis of scarring. The ability of the treatment to decrease significantly these factors is beneficial. Furthermore, a number of pro-inflammatory mediators were also observed to be decreased in the cells subjected to the treated versus control cells, while it was observed that certain anti-inflammatory cytokines were increased in the treated cells, for example IL-10.

b) Cell Proliferation (DHF Cell Cultures)

In reference to the data regarding growth factors induced upon the silicone-based biophotonic membrane of the present disclosure, as can be seen in Table 6 (above), the induced growth factors are mostly involved in blood vessel formation as opposed to being growth factors that are involved in cell proliferation. Furthermore, results from the cell proliferation assay performed in this Example 4 also show that the silicone-based biophotonic membrane did not induce cell proliferation. This lack of effect on fibroblast proliferation can be considered to be beneficial in hypertrophic scarring, given that hypertrophic scarring is characterized as a hyper-proliferative disorder.

c) In vivo Study Using a Dermal Fibrotic Mouse—Human Skin Graft Model System

Figure 5:
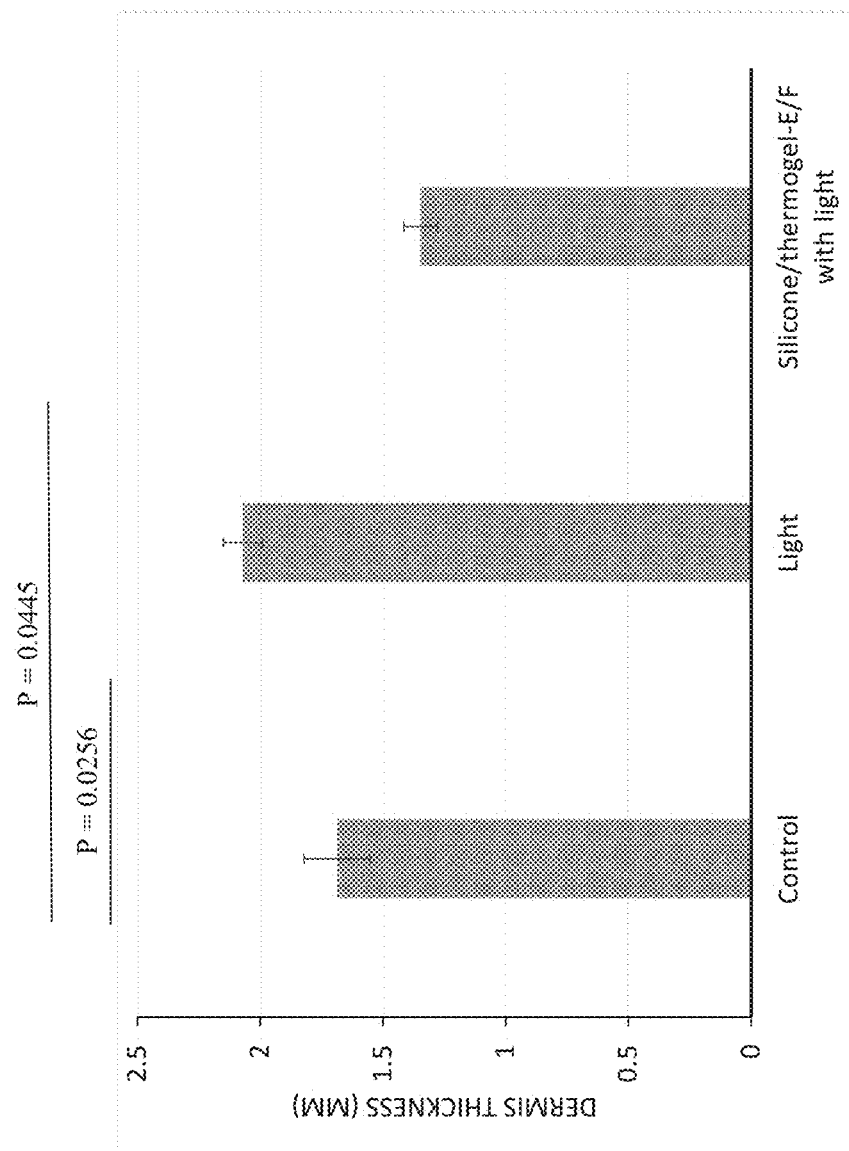
FIG. 5 illustrates a graph indicating a reduced dermal thickness of scars in a dermal fibrotic mouse-human skin graft model after treatment with a silicone-based biophotonic composition of the present description.

Morphologically, there were no visible significant differences between the groups grossly or in wound contraction measured by planimetery. However, by 4 weeks post-engraftment, significant reductions in scar thickness were measured histologically in the silicone-based biophotonic composition (applied as an unpolymerized gel)-plus-light and in the silicone-based biophotonic membrane-plus-light treatment groups as compared to both the control and light-only groups, ($1.35\pm0.07$, $1.35\pm0.08$ vs $1.69\pm0.13$, $2.07\pm0.08$ mm $P<0.05$) with improvements in re-epithelialization. These results are also presented in a graphical format in FIG. 5.

Figure 6:
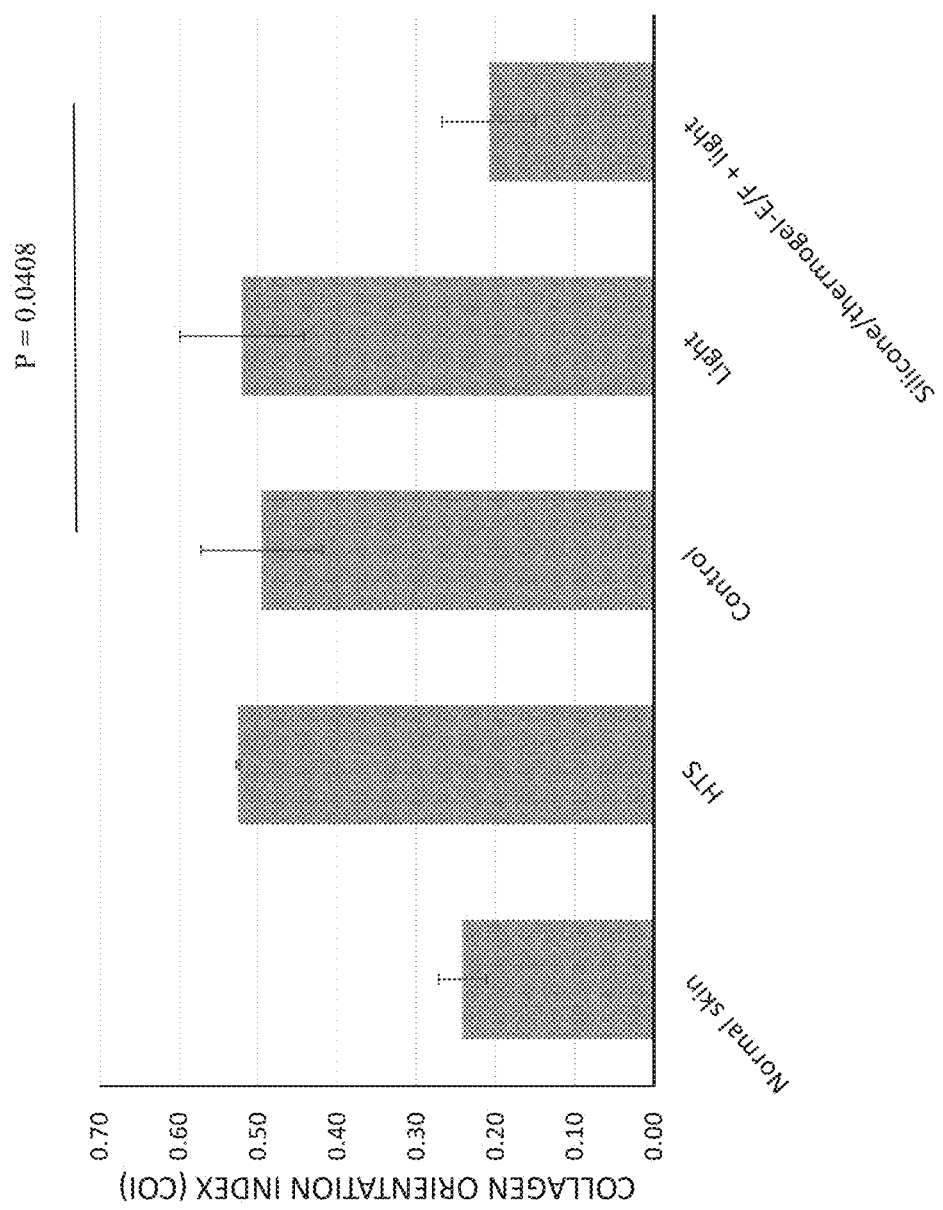
FIG. 6 illustrates a graph indicating an improved collagen remodeling, as measured with a collagen orientation index (COI), in a dermal fibrotic mouse—human skin graft model after treatment with a silicone-based biophotonic composition of the present description.

With respect to the effect of the treatments using the silicone-based biophotonic composition, morphological improvements in collagen fiber bundles and orientation (based on Masson Trichrome staining) were associated with accelerated collagen remodeling in the gel-plus-light and the membrane-plus-light treated groups versus the control and light-only groups (collagen orientation index, $0.18\pm0.04$, $0.21\pm0.06$ vs $0.50\pm0.08$, $0.52\pm0.08$. $P<0.05$). These results are also presented in a graphical format in FIG. 6.

Based on the above findings from the in vivo dermal fibrotic mouse—human skin graft model, these data indicate the potential for the silicone-based biophotonic composition of the present disclosure for acceleration of wound healing and reduction of fibrosis in human fibroproliferative disorders such as hypertrophic scarring.

It should be appreciated that the invention is not limited to the particular embodiments described and illustrated herein but includes all modifications and variations falling within the scope of the invention as defined in the appended claims.

The invention claimed is:

1. A silicone-based biophotonic membrane comprising a silicone phase and a thermogellable surfactant phase, wherein the thermogellable surfactant phase comprises at least one chromophore solubilized in a surfactant;
   wherein the silicone-based biophotonic membrane comprises between 80-99 wt % silicone phase and between 1-20 wt % thermogellable surfactant phase;
   wherein the silicone-based biophotonic membrane when exposed to actinic light having a wavelength of between about 400 nm and about 800 nm emits fluorescence;
   wherein the silicone-based biophotonic membrane has a light transmittance of between about 90% and about 100%: and
   wherein the silicone-based biophotonic membrane has a thickness of between about 0.5 mm and about 20 mm, a tensile strength of at least about 50 kPa, and a tear strength of from about 0.1 N/mm to about 5 N/mm.

2. The silicone-based biophotonic membrane of claim 1, wherein the thermogellable surfactant phase is emulsified in the silicone phase.

3. The silicone-based biophotonic membrane of claim 1, wherein the surfactant comprises a block copolymer, wherein the block copolymer comprises at least one hydrophobic block and at least one hydrophilic block.

4. The silicone-based biophotonic membrane of claim 1, wherein the surfactant comprises at least one sequence selected from the group consisting of polyethylene glycol-propylene glycol ((PEG)-(PPG)), polyethylene glycol-polylactic acid (PEG)-(PLA), polyethylene glycol-poly(lactic-c-glycolic acid) (PEG)-(PLGA), and polyethyelene glycol-polycaprolactone (PEG)-(PCL).

5. The silicone-based biophotonic membrane of claim 4, wherein the surfactant is a poloxamer.

6. The silicone-based biophotonic membrane of claim 1, wherein the thermogellable surfactant phase further comprises a surfactant selected from the group consisting of cetyl trimethylammonium bromide (CTAB) and sodium dodecyl sulfate (SDS).

7. The silicone-based biophotonic membrane of claim 1, wherein the chromophore is a cationic chromophore selected from the group consisting of cyanine, acridine and pyronine Y.

8. The silicone-based biophotonic membrane of claim 1, wherein the chromophore is Eosin Y.

9. The silicone-based biophotonic membrane of claim 1, wherein the thermogellable surfactant phase further comprises a stabilizer selected from the group consisting of gelatin, hydroxylethyl cellulose (HEC), carboxymethyl cellulose (CMC), and a thickening agent.

10. The silicone-based biophotonic membrane of claim 1, wherein the silicone phase comprises a polydimethylsiloxane polymer (PDMS).

11. The silicone-based biophotonic membrane of claim 10, wherein the content of the PDMS in the silicone phase is from about 5 wt % to about 100 wt %.

12. A method for biophotonic skin treatment, comprising:
   placing a silicone-based biophotonic membrane over a target skin tissue, wherein the silicone-based biophotonic membrane comprises a silicone phase and a thermogellable surfactant phase, and wherein the thermogellable surfactant phase comprises at least one chromophore solubilized in a surfactant; wherein the silicone-based biophotonic membrane comprises between 80-99 wt % silicone phase and between 1-20 wt % thermogellable surfactant phase; and wherein the silicone-based biophotonic membrane has a light transmittance of between about 90% and about 100%; and wherein the silicone-based biophotonic membrane has a thickness of between about 0.5 mm and about 20 mm, a tensile strength of at least about 50 kPa, and a tear strength of from about 0.1 N/mm to about 5 N/mm; and
   illuminating said silicone-based biophotonic membrane with light having a wavelength of between about 400 nm and about 800 nm; wherein the silicone-based biophotonic membrane when exposed to the actinic light having the wavelength that overlaps with the absorption spectrum of the at least one chromophore emits fluorescence.

13. The method of claim 12, wherein the skin treatment comprises treating a skin disorder selected from the group consisting of acne, eczema, psoriasis, and dermatitis.

14. The method of claim 12, wherein the skin treatment comprises promoting skin rejuvenation.

15. The method of claim 12, wherein the silicone-based biophotonic membrane is illuminated until the chromophore is at least partially photobleached.

16. A method for promoting wound healing comprising:
placing a silicone-based biophotonic membrane over a wound, wherein the silicone-based biophotonic membrane comprises a silicone phase and a thermogellable surfactant phase, and wherein the thermogellable surfactant phase comprises at least one chromophore solubilized in a surfactant; wherein the silicone-based biophotonic membrane comprises between 80-99 wt % silicone phase and between 1-20 wt % thermogellable surfactant phase; wherein the silicone-based biophotonic membrane has a light transmittance of between about 90% and about 100%; and wherein the silicone-based biophotonic membrane has a thickness of between about 0.5 mm and about 20 mm, a tensile strength of at least about 50 kPa, and a tear strength of from about 0.1 N/mm to about 5 N/mm; and
illuminating said silicone-based biophotonic membrane with light having a wavelength of between about 400 nm and about 800 nm; wherein the silicone-based biophotonic membrane when exposed to the actinic light emits fluorescence.

17. The method of claim 16, wherein the method comprises treating or preventing scarring.

* * * * *